United States Patent
Iniewski et al.

(10) Patent No.: US 11,701,065 B2
(45) Date of Patent: Jul. 18, 2023

(54) COMPTON SCATTERING CORRECTION METHODS FOR PIXELLATED RADIATION DETECTOR ARRAYS

(71) Applicant: REDLEN TECHNOLOGIES, INC., Saanichton (CA)

(72) Inventors: Krzysztof Iniewski, Coquitlam (CA); Saeid Taherion, Victoria (CA); Glenn Bindley, Vancouver (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 157 days.

(21) Appl. No.: 16/875,133

(22) Filed: May 15, 2020

(65) Prior Publication Data
US 2020/0367839 A1    Nov. 26, 2020

Related U.S. Application Data

(60) Provisional application No. 62/851,252, filed on May 22, 2019.

(51) Int. Cl.
*A61B 6/03*     (2006.01)
*G01T 1/161*     (2006.01)
(Continued)

(52) U.S. Cl.
CPC ............ *A61B 6/037* (2013.01); *A61B 6/4241* (2013.01); *A61B 6/4258* (2013.01);
(Continued)

(58) Field of Classification Search
CPC .. A61B 6/03; A61B 6/037; A61B 6/42; A61B 6/4208; A61B 6/4233;
(Continued)

(56) References Cited

U.S. PATENT DOCUMENTS

| | | | | |
|---|---|---|---|---|
| 5,841,140 A | * | 11/1998 | McCroskey | A61B 6/4258 250/363.04 |
| 6,242,745 B1 | * | 6/2001 | Berlad | G01T 1/2928 250/370.06 |

(Continued)

OTHER PUBLICATIONS

Anderson, S. E., "Event Classification For 3-D Position Sensitive Semiconductor Detectors," A dissertation submitted in partial fulfillment of the requirements for the degree of Doctor of Philosophy (Nuclear Engineering and Radiological Sciences) in The University of Michigan, 2011.

(Continued)

*Primary Examiner* — Allen C. Ho
(74) *Attorney, Agent, or Firm* — The Marbury Law Group PLLC

(57) ABSTRACT

Various aspects include methods compensating for Compton scattering effects in pixel radiation detectors. Various aspects may include determining whether gamma ray detection events occurred in two or more detector pixels within an event frame, determining whether the gamma ray detection events occurred in detector pixels within a threshold distance of each other in response to determining that gamma ray detection events occurred in two or more detector pixels within the event frame, and recording the two or more gamma ray detection events as a single gamma ray detection event having an energy equal to the sum of measured energies of the two or more gamma ray detection events located in a detector pixel having a highest measured energy in response to determining that the gamma ray detection events occurred in detector pixels within the threshold distance of each other.

20 Claims, 17 Drawing Sheets

(51) Int. Cl.
  *G01T 1/24* (2006.01)
  *G01N 23/20066* (2018.01)
  *G01N 23/046* (2018.01)
  *A61B 6/00* (2006.01)
  *G01T 1/164* (2006.01)

(52) U.S. Cl.
  CPC ......... *A61B 6/5205* (2013.01); *G01N 23/046* (2013.01); *G01N 23/20066* (2013.01); *G01T 1/1642* (2013.01); *G01T 1/249* (2013.01); *G01N 2223/051* (2013.01); *G01N 2223/063* (2013.01); *G01N 2223/1013* (2013.01); *G01N 2223/304* (2013.01); *G01N 2223/413* (2013.01)

(58) Field of Classification Search
  CPC ... A61B 6/4241; A61B 6/4258; A61B 6/4266; A61B 6/4275; A61B 6/52; A61B 6/5205; A61B 6/5258; A61B 6/5282; A61B 6/58; A61B 6/582; A61B 6/585; G01T 1/1642; G01T 1/24; G01T 1/242; G01T 1/243; G01T 1/246; G01T 1/247; G01T 1/249
  USPC ............ 378/19, 98.8, 189, 207; 250/363.01, 250/363.02, 363.03, 363.04, 363.05, 250/363.07, 363.08, 363.09, 363.1, 250/370.09
  See application file for complete search history.

(56) References Cited

U.S. PATENT DOCUMENTS

| | | | | |
|---|---|---|---|---|
| 6,388,258 | B1* | 5/2002 | Berlad | G01T 1/2928 250/363.02 |
| 6,590,215 | B2* | 7/2003 | Nygard | H04N 5/3456 348/E3.02 |
| 6,628,983 | B1* | 9/2003 | Gagnon | G01T 1/1648 600/431 |
| 6,791,090 | B2* | 9/2004 | Lin | G01T 1/242 250/336.1 |
| 7,180,074 | B1* | 2/2007 | Crosetto | G01T 1/1611 250/370.09 |
| 7,304,309 | B2* | 12/2007 | Suhami | G02B 6/1225 250/370.11 |
| 7,626,172 | B2* | 12/2009 | Takahashi | A61B 6/037 250/363.07 |
| 7,807,974 | B2* | 10/2010 | Ishitsu | A61B 6/037 250/363.04 |
| 7,817,827 | B2* | 10/2010 | Gal | A61B 6/4258 382/128 |
| 8,063,379 | B2* | 11/2011 | Suhami | G01T 5/02 250/370.09 |
| 8,076,645 | B2* | 12/2011 | Motomura | G01T 1/242 250/370.09 |
| 8,269,177 | B2* | 9/2012 | Kim | G01T 1/2985 250/363.04 |
| 8,450,692 | B2* | 5/2013 | Siegel | G01T 1/2985 250/362 |
| 8,466,418 | B2* | 6/2013 | Nakamura | G01T 1/1644 250/363.04 |
| 8,476,593 | B2* | 7/2013 | Degenhardt | G01T 1/2985 250/362 |
| 8,507,842 | B2* | 8/2013 | Liang | G01T 1/00 250/252.1 |
| 8,530,846 | B2* | 9/2013 | Cook | G01T 1/1648 250/363.01 |
| 9,024,262 | B2* | 5/2015 | Fukuchi | G01T 1/2985 250/362 |
| 9,332,952 | B2* | 5/2016 | Prevrhal | G01T 1/2985 |
| 9,535,175 | B2* | 1/2017 | Laurence | G01T 1/1647 |
| 9,872,664 | B1* | 1/2018 | Jin | A61B 6/4417 |
| 9,995,829 | B2* | 6/2018 | Degenhardt | G01T 1/00 |
| 10,371,834 | B2* | 8/2019 | Nelson | G01T 1/1611 |
| 10,390,775 | B2* | 8/2019 | Lage | A61B 6/4241 |
| 10,393,891 | B2* | 8/2019 | Iniewski | G01T 1/171 |
| 10,396,109 | B2* | 8/2019 | Iniewski | H03K 19/17716 |
| 10,502,845 | B2* | 12/2019 | Polf | A61N 5/1048 |
| 10,768,318 | B2* | 9/2020 | Qiang | G01T 1/208 |
| 10,925,554 | B2* | 2/2021 | Andreyev | A61B 6/037 |
| 10,928,527 | B2* | 2/2021 | Iniewski | G01T 1/249 |
| 10,935,675 | B2* | 3/2021 | Kuvvetli | G01T 1/247 |
| 10,952,698 | B2* | 3/2021 | Zhan | A61B 6/4241 |
| 10,989,676 | B2* | 4/2021 | Tanimori | G01T 1/2935 |
| 11,191,510 | B2* | 12/2021 | Liu | G01T 1/17 |
| 11,234,667 | B2* | 2/2022 | Andreyev | A61B 6/037 |
| 2017/0290555 | A1 | 10/2017 | Iniewski et al. | |
| 2017/0322319 | A1 | 11/2017 | Iniewski et al. | |

OTHER PUBLICATIONS

U.S. Appl. No. 16/155,786, filed Oct. 9, 2018, Redlen Technologies, Inc.
U.S. Appl. No. 16/185,963, filed Nov. 9, 2018, Redlen Technologies, Inc.
U.S. Appl. No. 16/199,588, filed Nov. 26, 2018, Redlen Technologies, Inc.
U.S. Appl. No. 16/659,096, filed Oct. 21, 2019, Redlen Technologies, Inc.

* cited by examiner

Compton Scattering for 350keV gammas, 7.5mm thick CZT detector

Compton Scattering for 122keV gamma, 6mm thick CZT detector

COMPTON SCATTERING CORRECTION METHODS FOR PIXELLATED RADIATION DETECTOR ARRAYS

FIELD

The present application relates generally to radiation detectors for computed tomography imaging systems, and more specifically to methods for correcting for Compton scattering effects in the output of pixelated radiation detectors.

BACKGROUND

In Single Photon Emission Computed Tomography (SPECT) imaging systems, gamma rays emitted from a source, such as a radiopharmaceutical or radiotracer, are detected by a detector array, such as a cadmium zinc telluride (CZT) detector. Other direct conversion detectors employing cadmium telluride (CdTe), gallium arsenide (GaAs), or silicon (Si), or any indirect director based on a scintillator material, may also be used in SPECT imaging systems. Images taken at different angles are joined together to reconstruct 3-dimensional images of the object under examination.

The electrical signal generated by solid state radiation detectors, such as CZT detectors, results from gamma-rays exciting electrons in the atoms of the material that ejects electrons from their orbits and into a conduction band of the bulk material. Each electron ejected into the conduction band leaves behind a net positive charge that behaves like a positively charged particle known as a "hole" that migrates through the material in response to an electric field applied between a cathode and an anode. Electrons in the conduction band are attracted by the resulting internal electric field and migrate to the anode where they are collected creating a small current that is detected by circuitry, while the holes migrate towards the cathode.

SUMMARY

Various aspects may include correcting for Compton scattering effects in a pixel radiation detector capable of registering detection events occurring in two or more detector pixels within an event frame by determining whether gamma ray detection events occurred in two or more detector pixels within an event frame, determining whether the detection events occurred in detector pixels within a threshold distance of each other in response to determining that detection events occurred in two or more detector pixels within the event frame, and recording the two or more detection events as a single detection event having an energy equal to the sum of the measured energies of the two or more detection events located in the detector pixel having a highest measured energy in response to determining that the detection events occurred in detector pixels within the threshold distance of each other. Some aspects further include ignoring or not recording the two or more detection events in response to determining that the detection events occurred in detector pixels separated by more than the threshold distance.

In some aspects, the threshold distance may be predetermined based upon an energy of gamma ray photons incident on the detector and a characteristic of pixel detectors in the detector. In such aspects, a characteristic of pixel detectors in the detector used in determining the threshold distance may include one or more of detector materials, detector thickness, detector pixel size, or separation distance between detector pixels. In such aspects, the threshold distance may be predetermined as a distance within a predefined fraction of Compton scattered photons will undergo another Compton scattering event or absorption via the photoelectric effect. In such aspects, the threshold distance may be predetermined terms of a number of detector pixels. Some aspects may further include determining whether an energy measured in any of the two or more detector pixels is within a Compton gap of gamma ray photons incident on the detector, and ignoring or not recording the two or more detection events in response to determining that the energy measured in any of the two or more detector pixels is within the Compton gap of gamma ray photons incident on the detector.

Various aspects of the present disclosure provide methods of compensating for Compton scattering effects in pixel radiation detectors, particularly SPECT imaging systems, by addressing through correction factors measurement effects caused by Compton scattering of gamma rays.

Various aspects may be used to calibrate solid state radiation detectors, such as CZT detectors, during design development, during manufacturing, and/or periodically in service.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

Various embodiments of the present disclosure include methods for processing outputs of pixilated radiation detectors used in gamma imaging systems, such as SPECT imaging, to improve accuracy by accounting for errors that could otherwise be introduced by Compton scattering of gamma ray photons within the detector materials. In particular, embodiment methods provide mechanisms for counting and allocating to particular detector pixels multiple photon-detector interaction events that are recorded in non-neighbor detector pixels within a brief duration or sampling window, referred to herein as an "event frame." The embodiment methods enable recording of photon-detector interaction events that begin with a Compton scatter interaction that otherwise would be ignored by conventional imaging systems, thereby increasing the efficiency of the detector system and enabling imaging to be accomplished with smaller amounts of radionuclide administered to the imaging subject.

Figure 1:
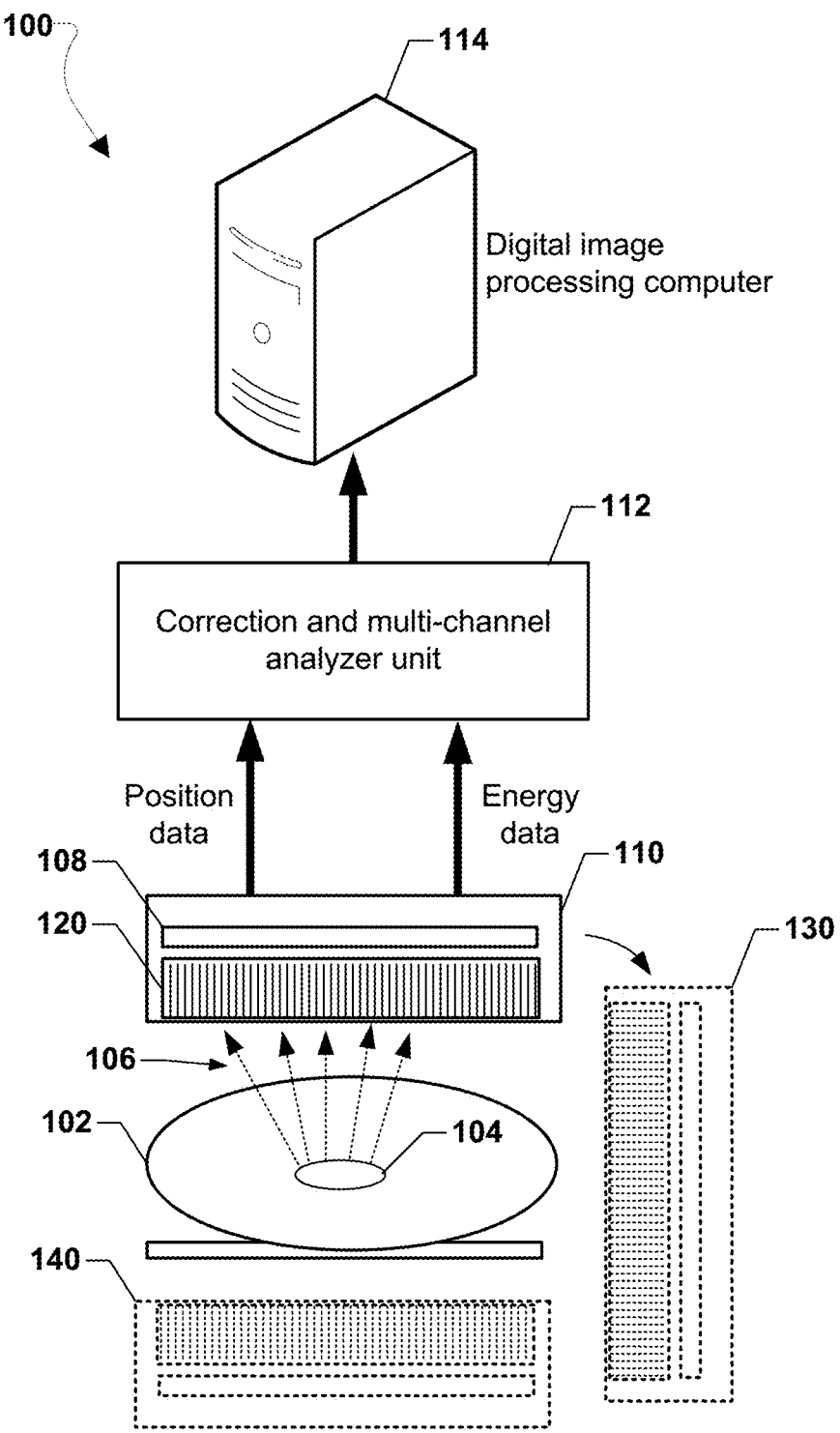
FIG. 1 is a block diagram of a Single Photon Emission Computed Tomography (SPECT) imaging system suitable for use with various embodiments of the present disclosure.

FIG. 1 is a functional block diagram of a SPECT imaging system 100. In a SPECT imaging system 100, a subject 102 (e.g., a patient) may be injected with a radiopharmaceutical containing a radioisotope, such as technetium 99, that is chemically configured to be absorbed by an organ or tumor to be examined creating a concentrated radiation source 104. The radiopharmaceutical within the source organ 104 emits gamma rays 106 that are detected by a digital radiation detector 108 within a gamma camera 110. Count and energy data from individual pixels within the digital radiation detector 108 are provided to an analyzer unit 112 that analyzes the detector data to determine the count and energy spectrum of detected gamma rays 106 and provides the analyzed data to a digital imaging system computer 114. The analyzer unit 112 may apply calibration corrections including, for example, corrections for charges shared between pixels is determined according to various embodiments.

The SPECT imaging system 100 may also include additional structures, such as a collimator 120 within the gamma camera 110 and a robotic mechanism (not shown) that is configured to position the gamma camera 110 over the subject 102 at a variety of orientations (as illustrated in 130 and 140). Positioning the gamma camera 110 at various orientations with respect to the subject 102 enables gamma ray count and energy data to be acquired by the digital radiation detector 108 from several different angles. Data collected in this manner can then be processed by the digital image system computer 114 to construct a 3D image of the organ or tumor 104 where the radiopharmaceutical has accumulated.

Various alternatives to the design of the SPECT imaging system 100 of FIG. 1 may be employed to practice embodiments of the present disclosure. For example, in industrial applications, such as luggage screening, the gamma source 104 may be positioned on a far side of the object being scanned with respect to the gamma camera 110 and the gamma photons imaged by the digital radiation detector 108 may be photons that have passed through the object instead of being emitted from the object. In such applications, the gamma source 104 and gamma camera 110 may be both rotated about the object, such as on a rotating frame or gantry. Further, various other types of systems that include a gamma camera 110 that uses a solid-state pixilated digital radiation detector 108 may benefit from various embodiments, particularly for calibrating the digital radiation detector 108 during manufacture or in service.

The digital radiation detector 108 of a SPECT imaging system 100 may include an array of radiation detector elements, referred to as pixel detectors. The signals from the pixel detectors may be processed by a pixel detector circuit, such as an analyzer unit 112, which may sort detected photons into energy bins based on the energy of each photon or the voltage generated by the received photon. When a gamma photon is detected, its energy is determined and the photon count for its associated energy bin is incremented. For example, if the detected energy of a photon is 64 kilo-electron-volts (keV), the photon count for the energy bin of 60-80 keV may be incremented. The number of energy bins may range from one to several, such as two to six. The greater the total number of energy bins, the better the energy spectrum discrimination. Thus, the detector 106 of a gamma camera 110 provides information regarding both the location (within pixels) of gamma photon detections and the energy of the detected gamma photons.

Some SPECT imaging systems provide full body diagnostics such as may be useful for oncology diagnostics. Such SPECT imaging systems may be configured to localize precisely activity spots while providing a large field of view, such as sufficient to fit the whole body. Such SPECT full body imaging application may benefit from use of isotopes other than or in conjunction with Tc99m, as listed in Table 1.1 below. As such, detectors used for SPECT full body imaging application may be configured to detect gamma rays with energies ranging from 70 keV (Tl-201) on the low end to 364 keV (I-131) on the high end. In practice, 30-400 keV range is recommended.

TABLE 1.1

List of commonly used SPECT isotopes

| Isotope | Half-life | Main γ-emissions | Photon aboundances | Examples of clinical applications |
|---|---|---|---|---|
| Tc-99 m | 6 h | 140 keV | 89% | brain, heart, liver, lungs, bones, cancer, kidneys, throid |
| Ga-67 | 3.26 d | 93 keV | 38% | abdominal infection, |
|  |  | 185 keV | 21% | lymphoma, cancer |
|  |  | 300 keV | 17% | imaging |
| In-111 | 2.80 d | 171 keV | 91% | Infections, cancer |
|  |  | 245 keV | 94% | imaging |
| I-123 | 13.2 h | 159 keV | 83% | throid, brain, heart metabolism, kidney |
| I-131 | 8.02 d | 364 keV | 81% | thyroid, cancer imaging, metastasis detection, brain |
| Tl-201 | 3.04 d | 70 keV | X-rays | myocardial |
|  |  | 167 keV | 11% | perfusion |
| Xe-133 | 5.24 d | 81 keV | 37% | lung ventilation, brain imaging, cerebral blood flow |

Gamma-ray photons can interact with the detector materials (e.g., CZT crystal) in various ways. Gamma-ray photons may be completely removed from the incident photon beam by absorption in a process known as the photoelectric effect, may be scattered by Compton scattering or Rayleigh scattering, or may pass through the CZT detector without any interaction or deterioration of their energy. At low energies of interests, such as below 200 keV, and typical sensor thickness of 5 mm, most of the incoming radiation photons are either absorbed or scattered, the relative portion of each effect being highly dependent on the incoming photon energy.

The following three absorption and scattering effects are the most relevant: the photo-electric effect; Rayleigh scattering; and Compton scattering. The effective photon cross section in CZT of each effect is plotted in the graph 200 that is FIG. 2. Photo-electric effect (202) is dominant in the considered energy range of 20 to 200 keV, which is typical for medical imaging. Rayleigh scattering 204 is a dominant form of scattering at lower energies. At higher energies Compton scattering 206 becomes more probable. For example, a gamma-ray photon with an energy of 122 keV will interact with a CZT radiation detector via the photo-electric effect with an 82% probability, via the Rayleigh scattering with a 7% probability, and via the Compton scattering with a 11% probability. Due to the energy dependency of the cross sections for these three types of interactions, charge-sharing correction methods of various embodiments work the best at energies below 200 keV, working less well at higher energies due to Compton scattering.

How much of a gamma-ray photon's energy will deposit in a given radiation detector pixel is dictated by which interaction mechanism occurs, which is in turn dependent on the energy of the photon and the average atomic number of the crystal. For the average atomic number of the CZT sensor (49.1) the primary interaction mechanism with standard Tc99m isotope (140 keV) is photoelectric effect absorption as illustrated in the graph shown in FIG. 2. However, for energies higher than 280 keV the Compton effect dominates and obviously can no longer be neglected.

In the photo-electric effect, the energy of the interacting photon is absorbed by an electron that is ejected (referred to as a "photo-electron") from its atom and the photon effectively disappears after the interaction. The energy of the photo-electron is quickly dissipated by losing energy through electron-electron scattering interactions with electrons within the detector materials, which generates a cloud of electrons that is collected by an anode 406a, thereby enabling detection of the photon and a measurement of the photon's energy. A complete absorption of the photon energy is the desired effect for CZT imaging. The name "photo-electron" comes from a process of ejecting an electron from one of the atomic shells of CZT. After the ejection of the photo-electron the atom is ionized. The vacancy in the bound shell is refilled with an electron from the surrounding medium or from an upper atom shell. This may lead either to the emission of one or more characteristic fluorescence X-rays or to the ejection of an electron from one of the outer shells called an Auger electron.

Depending whether tellurium, cadmium or zinc atoms are involved, the resulting fluorescence X-ray energies might be in an 8 to 31 keV range (Te 27-31 keV; Cd 23-26 keV; Zn 8-10 keV). Therefore, in practical terms soft X-rays events may be detected if the detection threshold is at least 31 keV, which is typically the case. This is particularly true in single-photon emission spectroscopy (SPECT) that uses standard isotopes like Technetium ($^{99m}$Tc) that emits a 140 keV photon. In addition, the projected distance that the fluorescence X-rays may travel in CZT is about 0.1 mm, which is much smaller than the typical pixel size of 2 mm. Therefore, while fluorescence generated soft X-rays might show up in the tail of the measured CZT spectrum, such signals will likely not contribute significantly to charge sharing between pixels. However, it is worth noting that the generation of soft-X rays affects the measured spectrum indirectly because the system will measure the energy of the absorbed photon as being less than the actual γ-photon energy by the amount of energy in the soft X-rays, thereby distorting the measured spectrum of radiation.

Rayleigh scattering involves photon scattering by atoms as a whole, frequently also called coherent scattering as the electrons of the atom contribute to the interaction in a coherent manner so that there is no energy transferred to the CZT material. The elastic scattering process changes only the direction of the incoming photon. Rayleigh scattering is a rather negligible effect in CZT SPECT imaging as it will not affect the measured energy spectrum, although it may lower the camera efficiency a bit.

Figure 3:
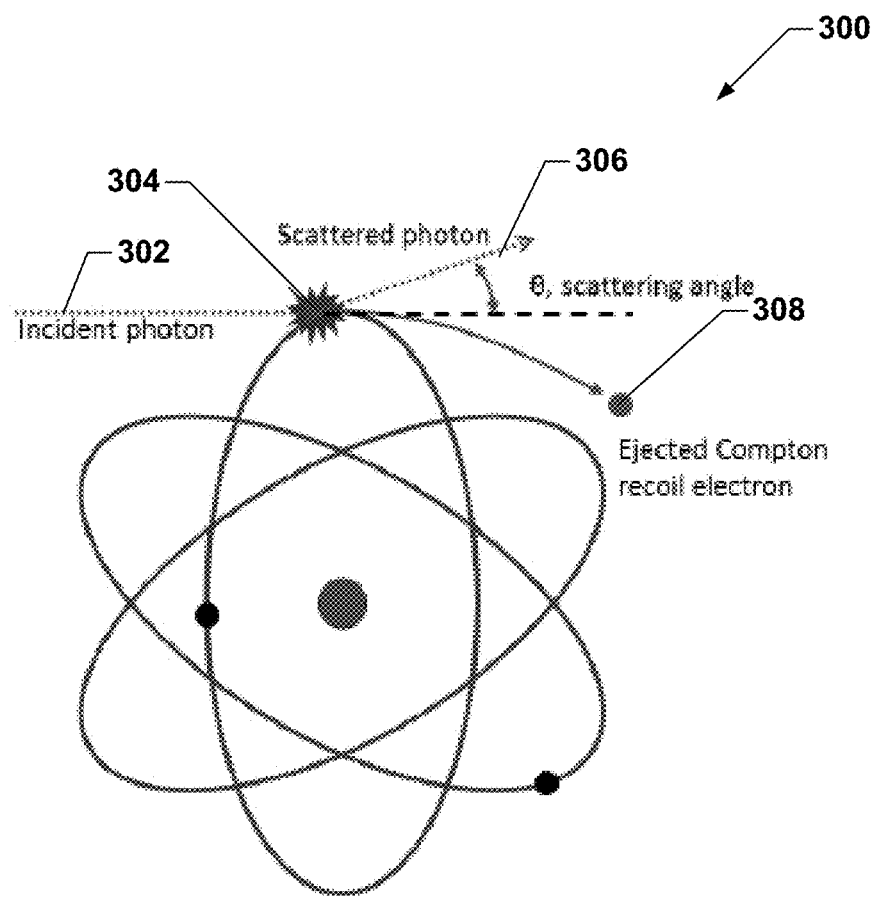
FIG. 3 is a concept diagram of a Compton Scattering gamma ray interaction with an election within an atom.

Unlike the photoelectric effect, Compton scattering does not result in elimination of the original incident photon but rather deflects it with a scattering angle θ thus generating a new electron called the Compton recoil electron. Compton scattering involves photons that are scattered by electrons and as a result lose some of their primary energy but continue to travel through the detector material, albeit along a redirected path. As illustrated in FIG. 3, Compton scattering 300 occurs when an incoming photon 302 imparts some of its energy to an electron in a scattering event 304. The energy imparted to the electron is in the form of kinetic energy, ejecting the electron 308 from the atom. The resulting lower energy photon 306 is scattering through an angle θ. The energy and momentum lost by the incoming photon 302 is transferred to the recoil electron 308, which is emitted at an angle with respect to the direction of the incoming photon.

The Compton Scattering mechanism can contribute significantly to the energy spectrum of gamma-ray photons measured by a CZT detector. The decrease in the photon energy that occurs in a Compton scattering event increases with increasing scattering angle θ. The Compton scattering equation describes the change in photon energy and its corresponding wavelength as:

$$\lambda' - \lambda = \frac{h}{m_e c}(1 - \cos\theta)$$

where $\lambda$ is the wavelength of the photon before scattering, $\lambda'$ is the wavelength of the photon after scattering, $m_e$ is the mass of the electron, θ is the angle by which the photon's trajectory differs from the original direction of the incident photon (referred to as the scattering angle), h is Planck's constant, and c is speed of light. Substituting textbook values for $m_e$, c and h, the characteristic Compton wavelength, defined as $h/(m_e c)$, is found to be equal to 2.4 picometers (pm).

Solving for the scattered photon energy in terms of the scattering angle yields the following equation:

$$E'_p = \frac{E_p}{1 + (E_p/m_0 c^2)(1 - \cos\theta)} \quad [\text{Eq 1}]$$

The kinetic energy of the recoil electron is therefore:

$$E_{o^-} = E_p - E'_p \quad [\text{Eq 2}]$$

As equations 1 and 2 reveal, the recoil electron 308 has a maximum kinetic energy when the scattering angle is 180 degrees to the original direction of the incident photon, which is referred to as the so-called Compton edge. As illustrated in the graph 600 in FIG. 6, the Compton edge is frequently visible in the spectrum measured by a CZT radiation detector as an abrupt end 604 to the energy tail 610 caused by Compton scattering.

For the SPECT application, the highest intensity of Compton scattered photons would be toward the forward or backward direction (i.e., scattering angles of approximately 0 degrees or approximately 180 degrees to the original direction of the incident photon), with a minimum at a 90-degree scattering angle.

Compton scattering can lead to statistical errors in SPECT detection as discussed below. This is because Compton scattering results in a detection event generated in that detector pixel due to the recoil electron and a scattered photon. At each site of a Compton scatter interaction, a recoil electron will lose energy by exciting electrons in nearby atoms into the conduction band creating electron-hole pairs, thereby generating a cloud of electrons that will be collected by the pixel anode. However, some scattered photons will leave the detector, taking with them part of the energy of the incoming photon, and as a result the amount of energy recorded from that photon will be limited to that of the recoil electron from the Compton scattering event. Some scattered photons will interact with the detector material by the photoelectric effect (i.e., absorption) or another Compton scatter interaction in another (adjacent or nonadjacent), and as a result, the energy of the incoming photon will be distributed between two (or more) different detector pixels. Further, some scattered photons will undergo a sequence of Compton scattering interactions, each resulting in a recordable event of different energies at different locations (i.e., different detector pixels) in the detector. Thus, a single incoming photon 302 may result in one or more scattered photons that may interact with detector material in several detector pixels, with each event recorded as a fraction of the energy of the initial photon. If Compton scatter interactions are ignored (e.g., by energy gating to above the Compton gap), then the efficiency of the detector will be significantly reduced.

The Compton equation has two interesting properties. First, the characteristic Compton wavelength value is small compared to typical gamma ray wavelengths used in medical imaging (the wavelength of a 100 keV gamma ray is about 12 pm). As the result, the maximum wavelength change due to Compton scattering is only a fraction of the original wavelength. Secondly, the largest change in the photon energy can only be expected for scattering angles θ close to 180 degrees. Thus, the maximum wavelength change is twice the Compton wavelength change.

Compton scattering also occurs within the imaging subject in SPECT as well as in surrounding structures and the camera itself, raising the problem of distinguishing gamma photons that are coming from the subject of the imaging from gamma photons scattered off of other structures. Small angle Compton scattering diverts gamma photons through a small angle that may be acceptable for imaging, but reduces the gamma photon energy by only a small amount. In contrast, large angle Compton scattering, which would interfere with imaging, reduces the gamma photon energy by a significant amount.

In normal circumstances, all photon scattering angles will occur in the detector. Therefore, a continuum of energies can be transferred to the electron, ranging from:

$$\theta \cong 0 \quad [\text{Eq 3}]$$

$$E'_p \cong E_p$$

$$E_{o^-} \cong 0$$

to $$\theta = \pi \quad [\text{Eq 4}]$$

$$E'_p \big|_{\theta=\pi} = \frac{E_p}{1 + (2E_p/m_0 c^2)}$$

$$E_{o^-} \big|_{\theta=\pi} = E_p \frac{2E_p/m_0 c^2}{1 + (2E_p/m_0 c^2)}$$

Figure 4A:
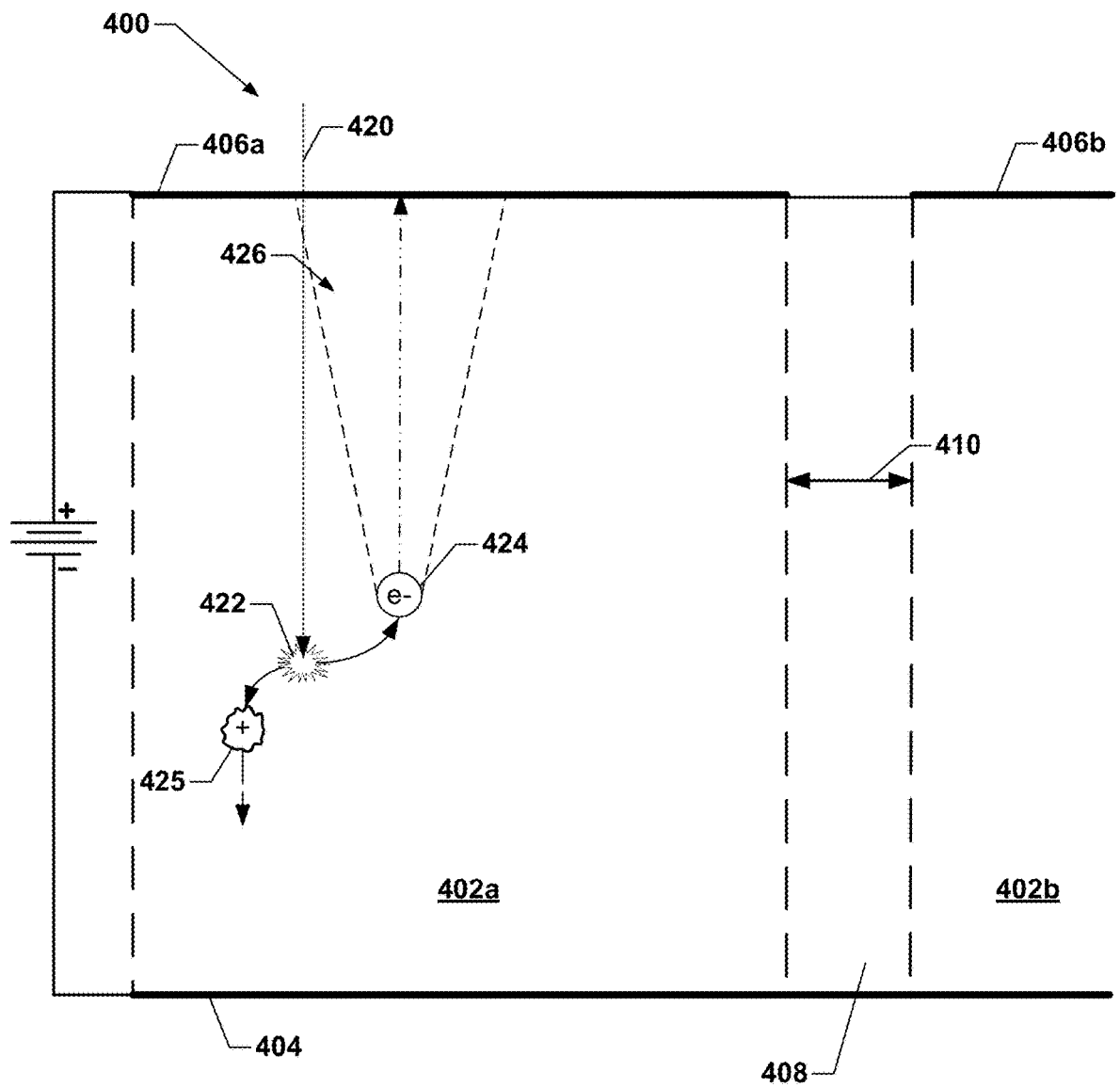
FIG. 4A is a conceptual cross section view diagram of a semiconductor pixel radiation detector illustrating a gamma-ray absorption and mechanisms for detecting and measuring the energy of the detected gamma-ray.

As an γ-ray photon enters the CZT sensor volume of a detector and interacts with the atoms constituting that sensor it will deposit some, or all, of its energy. FIG. 4A illustrates a cross-sectional view of two pixels 402a, 402b within a CZT radiation detector array 400. Such a detector 400 may include a sheet of CZT semiconductor crystal 408 on which are applied to a cathode 404 and the anodes 406*a*, 406*b* that define each pixel 402*a*, 402*b*. The anodes 406*a*, 406*b* may be spaced apart by an inter-pixel gap 410. In typical radiation detector arrays 400, the thickness of the CZT semiconductor crystal 408 may range from 1 mm to 20 mm, the anodes 406*a*, 406*b* may have a side dimension of 0.1 mm to 3 mm, and the inter-pixel gap 410 may range from 0.01 mm to 0.5 mm.

When a gamma-ray 420 is absorbed via a photoelectric effect event 422 by an electron of an atom within the CZT semiconductor crystal 408, the energy of the photon is transferred to an ejected electron (not shown) that quickly slows down by ionizing nearby atoms thus generating a cloud of electrons 424 ejected into the conduction band of the semiconductor along the path of travel. The range of a photoelectron in CZT depends on the energy carried off by that electron. Each ejected electron creates a corresponding hole 425 of positive charge. The clouds of electrons (and holes) generated by a photoelectron are not uniform in charge density, because electron-hole production increases towards the end of the track of the photoelectron. A voltage is applied between the cathode 424 and anodes 406*a*, 406*b* causes the electrons 424 to drift to the anode 406*a* where they are collected as a signal as described above. Holes 425 similarly migrate towards the cathode 404. Diffusion and charge repulsion forces cause the electron cloud to expand (as shown at 426) by the time the electrons reached the anode 406*a*.

The term "cloud" is used to highlight the fact that the physical size of the electron charge is not a point but approximately a sphere with a certain radius. Each g-ray photon absorbed in the CZT detector generates several thousands of electrons, so even the initial charge has finite physical dimensions. The number of generated electrons can be estimated by dividing the incoming photon energy by the CZT ionization energy of 4.64 eV. For example, a Technetium 99 gamma ray photon with an energy of 140 keV will produce about 30,000 electrons in the conduction zone, collectively carrying a charge of approximately 4.8 femto coulombs (fC).

Figure 4B:
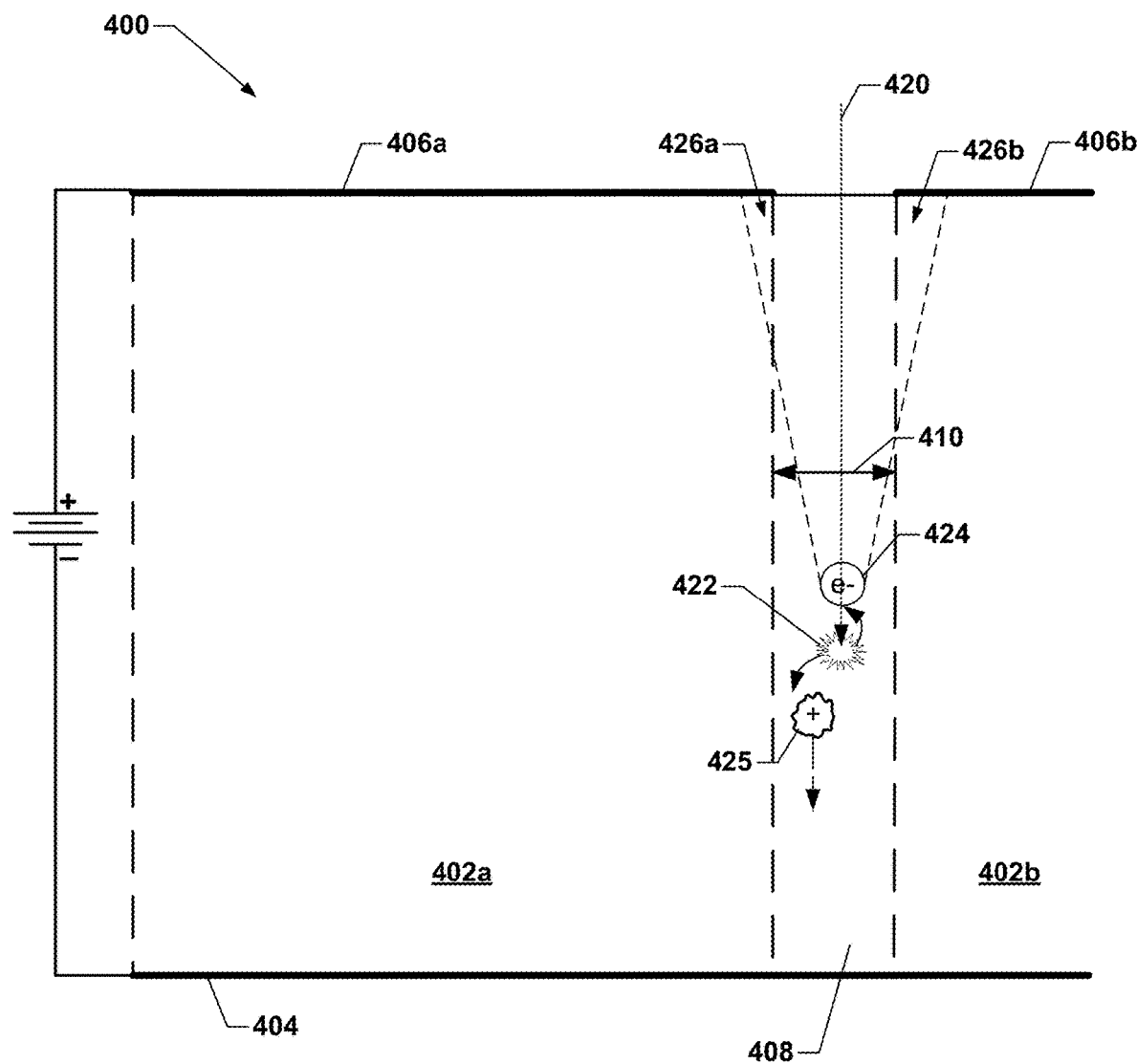
FIG. 4B is a conceptual cross section view diagram of a semiconductor pixel radiation detector illustrating a gamma-ray absorption occurring between adjacent detector pixels and the effect of measuring the energy of the detected gamma-ray between adjacent pixels.

Because the energy of the incident photon 420 is reflected in the number of electrons in the cloud that are collected by the anodes 406*a*, 406*b*, the location of detection events and the measured energy of such events depends upon the location in the detector where energy is deposited from various photon-matter interactions. For example, as illustrated in FIG. 4B, a gamma ray photon 420 entering the detector 400 near the boundary of a detector pixel or within the inter-pixel gap 410 and undergoing a photoelectric absorption interaction 422 will result in a cloud of electrons 424 (and holes 425) that will be motivated by the electric field generated by the neighboring anodes 406*a*, 406*b*. Thus, as the electron cloud 424 drifts towards the anodes 406*a*, 406*b*, expanding due to mutual repulsion, a portion 426*a* of the electrons will be collected by one anode 406*a* and a portion 426*b* of the electrons will be collected by the neighboring anode 406*b*. Also, some electrons in the cloud 424 may interact with surface effects within the gap 410 between anodes 406*a*, 406*b*, and not be collected by either anode. Thus, a gamma ray photon 420 entering the detector 400 near the boundary of a detector pixel or within the inter-pixel gap 410 will result in signals in two detector pixels 402*a*, 402*b*, with each measured signal being a fraction of the total charge (i.e., electron cloud 424) created by the photoelectric effect interaction 422. Similar effects occur for Compton scattering events that occur near the boundary of a detector pixel or within the inter-pixel gap 410 with the added effect that the amount of charge generated depends on the angle of scattering and is less than the Compton edge (see FIG. 6).

Figure 5:
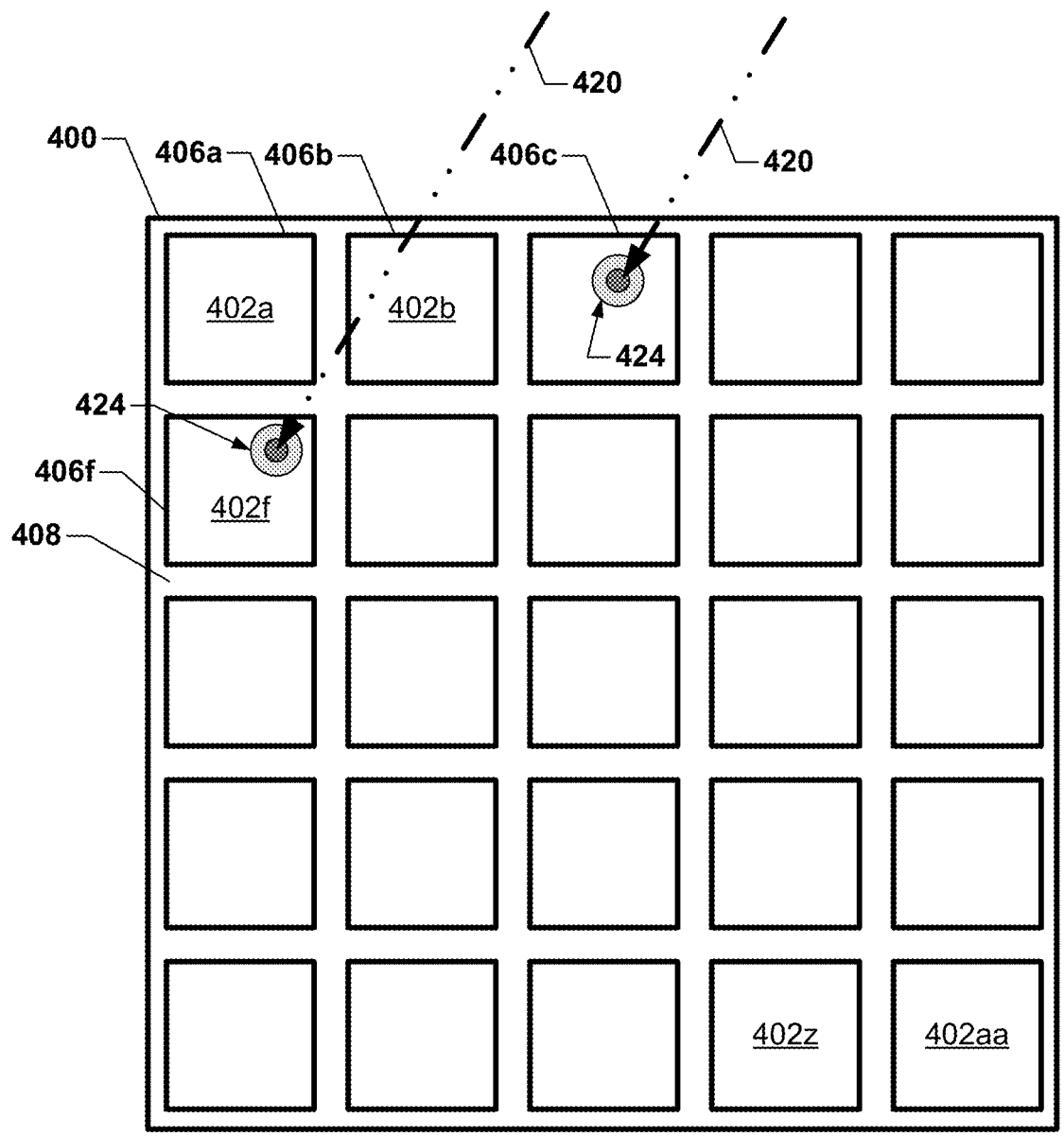
FIG. 5 is a conceptual top view diagram of a semiconductor pixel radiation detector illustrating gamma-ray interactions.

FIG. 5 is a top view of a portion of a pixelated radiation detector array 400 showing the plurality of pixels 402*a*-402*aa* formed by the anodes 406*a*, 406*b* positioned on the CZT semiconductor crystal 408. As described above, when a gamma-ray 420 interacts with atoms within the CZT semiconductor crystal 408, the cloud of ejected electrons 424 are gathered on the nearby anode 406*c*, 406*f* and recorded as a count. Further, the number of electrons 424 (i.e., charge) collected on the anode 406*c*, 406*f* is reflective of the energy of the incoming photon, and thus a measurement of the energy (or spectrum) of the detected photon can be determined from the charge or current detected on the anodes.

Figure 6:
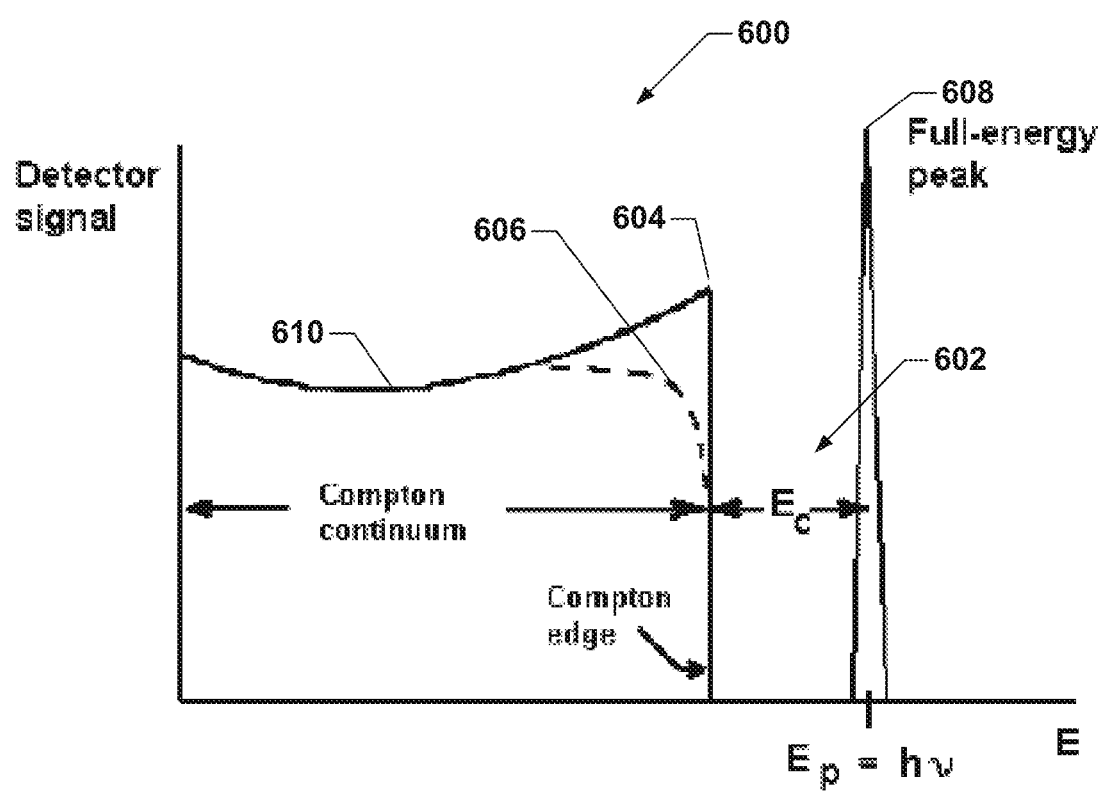
FIG. 6 graph of the detected signal of gamma-ray interactions with a radiation detector showing the effects on measured energy due to Compton scattering.

As illustrated in FIG. 6, gamma-ray photons that are absorbed by the photoelectric effect will result in a sharp peak in energy 608 reflective of the photon's energy, while Compton scattering results in a continuum of energies 610 transferred to the Compton recoil electron depending on the scattering angle, ranging from 0 to 180 degrees. In various embodiments, the electrons are assumed to be initially free or unbound. In actual detector materials, the binding energy of the electron can have a measurable effect on the shape of the Compton continuum at lower photon energies. This effect can be a rounding of the rise in the continuum near the Compton edge (illustrated by the dashed line 606). In FIG. 6, the gap 602 between the maximum Compton recoil electron energy 604 and the incident photon energy 608 is given by:

$$E_c = E_p - E_{\odot^-}|_{\theta=\pi} = \frac{2E_p}{1 + (2E_p/m_0c^2)} \quad [\text{Eq 5}]$$

Figure 7:
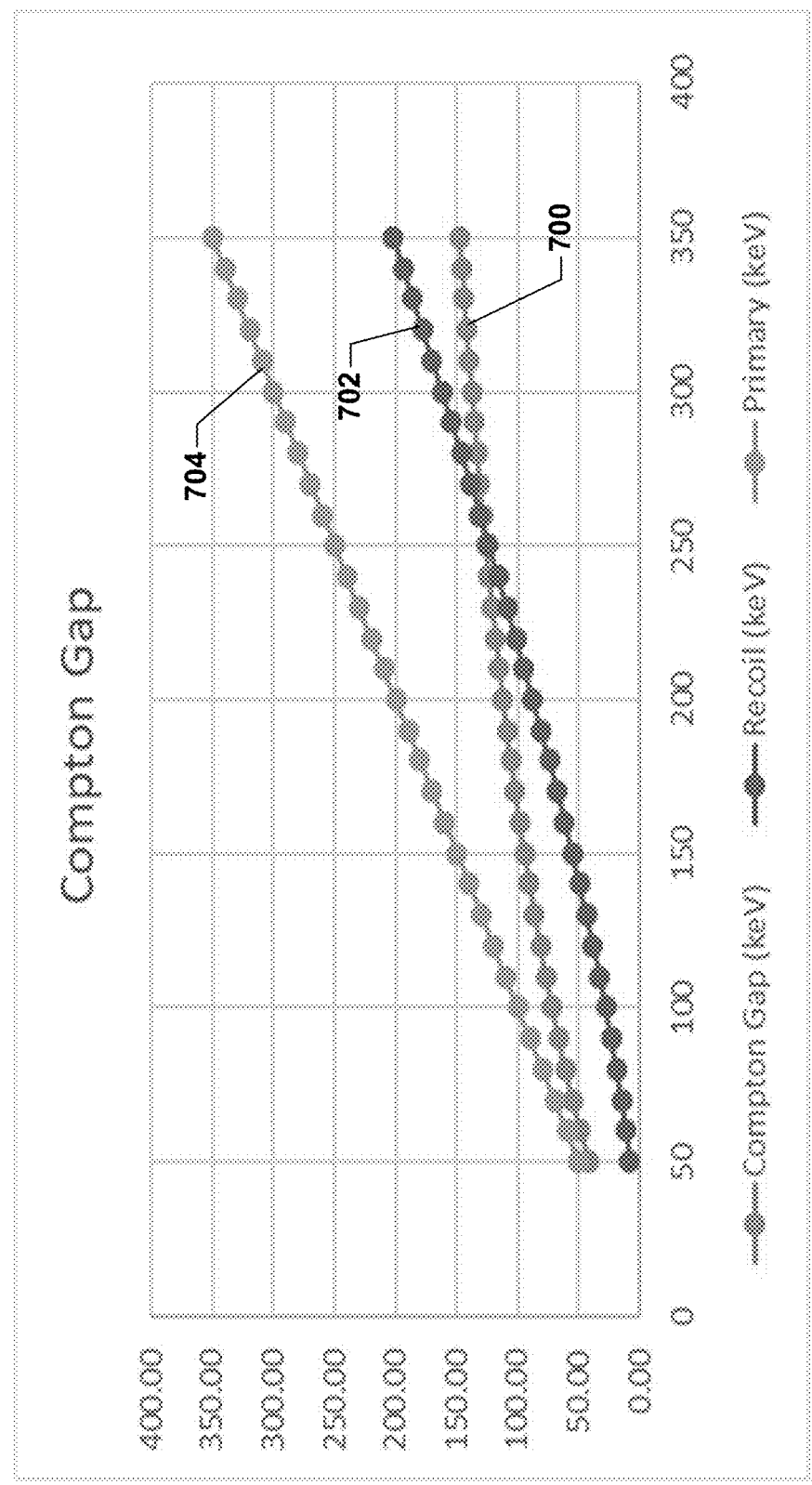
FIG. 7 is a graph illustrating the correlation between gamma-ray photon energy and the Compton Gap and recoil electron energy.

If the incident photon energy is large (Ep>>m0c2), then this energy difference, also called Compton gap 602, approaches a constant value given by $\frac{1}{2} \ast m_0 c^2$ which is 255.5 keV. This limit however is not reached in SPECT. For the primary photon range between 50 keV and 350 keV the recoil energy ranges from 8 keV to 202 keV while the Compton gap increases from 42 keV and 148 keV. This is illustrated in FIG. 7, which shows how the Compton gap 700 and recoil electron energy 702 vary with the incident photon energy 704.

After a Compton scattering event in the detector material, the scattered photon either interacts with the detector or escapes from it. Two situations are considered.

Figure 8A:
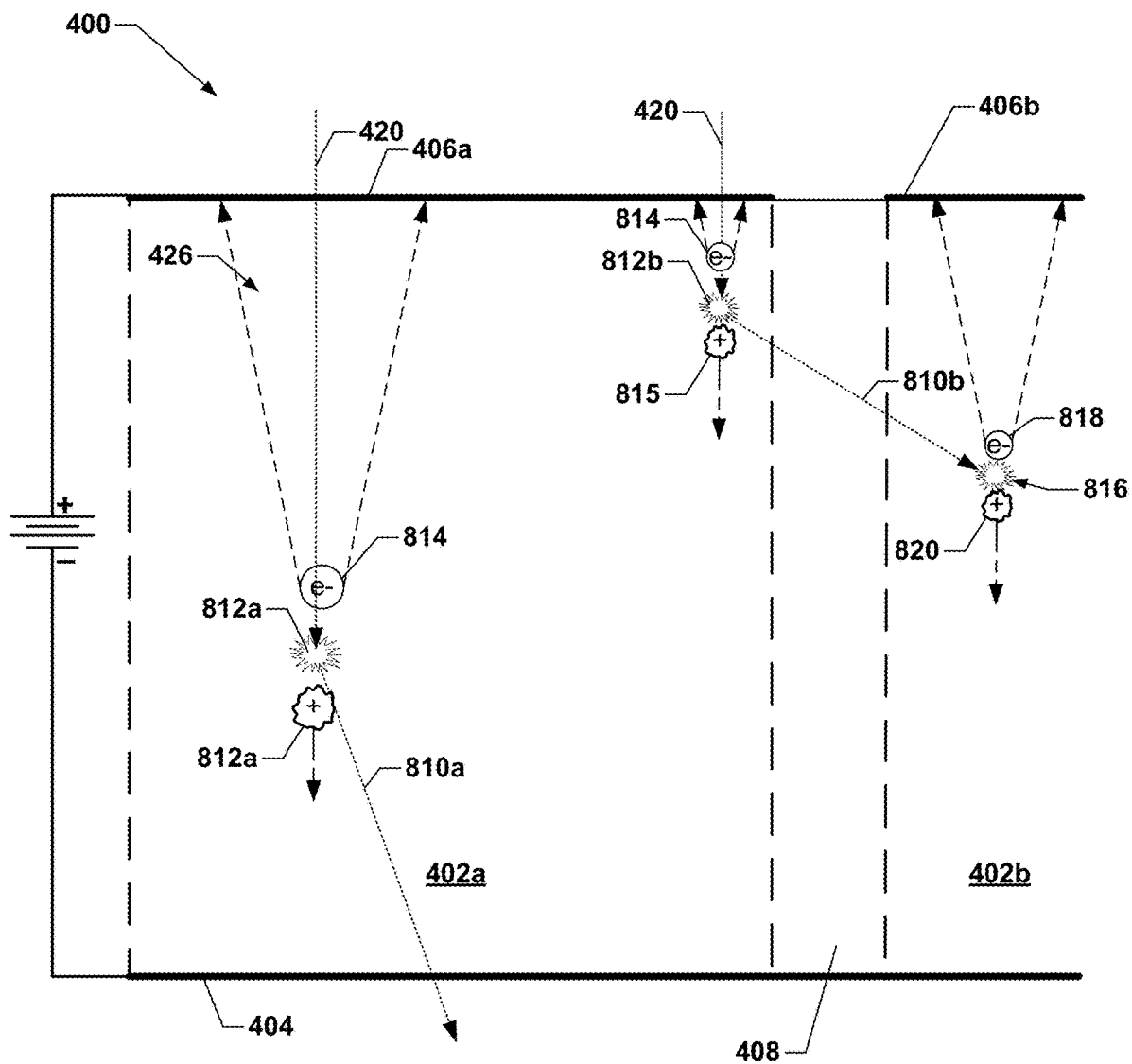
FIG. 8A is a diagram illustrating the detection and energy measurement mechanisms for gamma-ray detection with and without Compton scattering of detected photons.

In a first situation illustrated in FIG. 8A, after the Compton scattering event 812, the scattered photon 810*a* leaves the detector 402*a*. In this situation an incident gamma-ray photon 420 experiences a Compton scattering event 812*a*, which generates a recoil electron that quickly loses its energy by generating an electron cloud 814 that is captured by the anode 406*a* and a cloud of holes 815, and a scattered photon 810*a* that leaves the detector pixel 402*a*. When the scattered photon 810*a* leaves the detector, the energy of the escaped photon will be lost from the detector (i.e., not recorded). However, the scattered photon 810*b* may leave one detector pixel 402*a* and be absorbed via a photoelectric effect event 422 in another pixel detector 402*b*, which generates an electron cloud 818 and hole cloud 820 that are measured by that pixel detector 402*b*. Thus, in the Compton scattering event 812b, the full energy of the incoming gamma-ray photon 420 is measured partly by one pixel detector 402a and partially by an adjacent pixel detector 402b. These situations in which the Compton scattered photon leaves the pixel detector contributes to the energy spectrum of the photon measured by the pixel detector illustrated in FIG. 6.

Figure 8B:
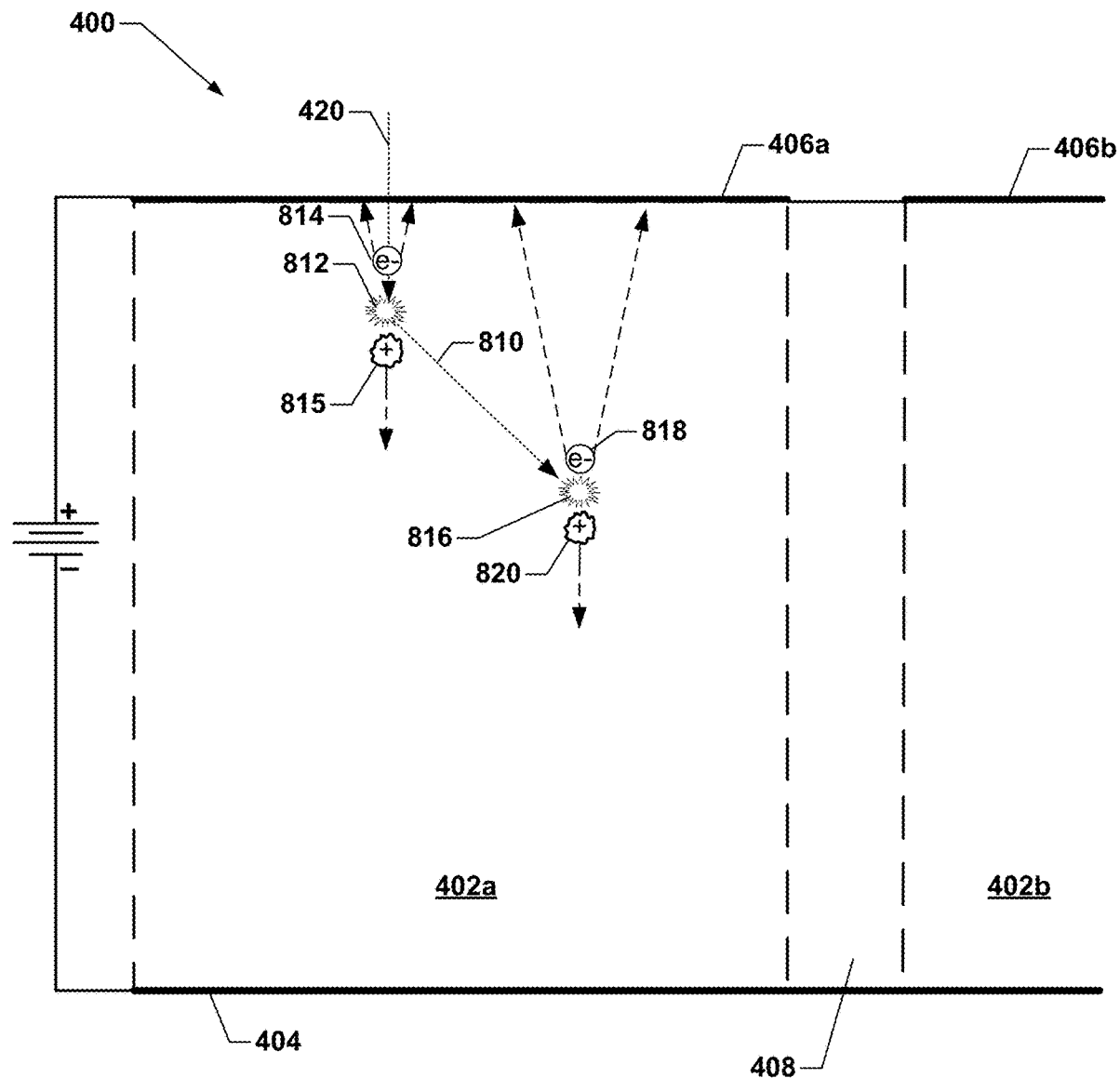
FIG. 8B is a diagram illustrating the detection and energy measurement mechanisms for gamma-ray detection in which Compton scattering results in partial measurement of a gamma-ray photon energy in an adjacent detector.

In a second situation illustrated in FIG. 8B, multiple scattering events occur for a single gamma-ray photon 420 within a single detector pixel 402a. In the case of multiple scattering, the Compton scattered photon 810 also interacts within the detector pixel 402a in which a Compton scattering event 812 occurs, either by additional Compton scatterings or by a photoelectric effect event 816. Thus, two (or more) electron clouds 814, 818 and two hole clouds 815, 820 may be formed in one detector pixel 402a. In this situation the full energy of the energy of the incoming photon will end up in the detector crystal and measured by the cathode 406a of a single detector pixel 402a, which contributes to the full energy peak signal 608 at $E=E_p$ of the photon energy spectrum illustrated in FIG. 6.

Figure 8C:
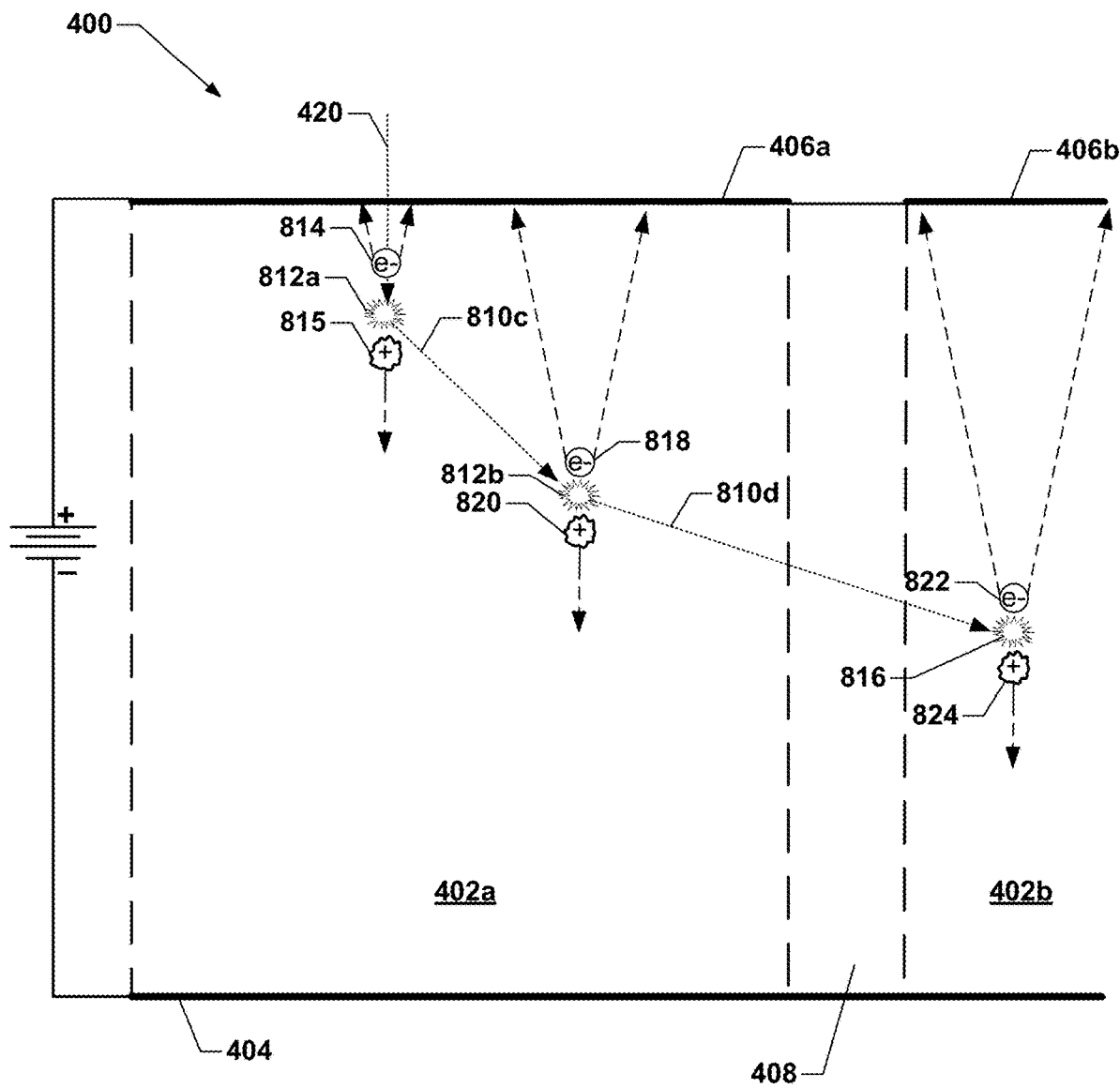
FIG. 8C is a diagram illustrating the detection and energy measurement mechanisms for gamma-ray detection in which multiple Compton scattering events occur before a photoelectric effect event.

An incident gamma ray photon 420 may result in multiple Compton scattering events as illustrated in FIG. 8C. In the illustrated example, an incident gamma ray photon 420 interacts with a detector pixel 402a in a first Compton scattering event 812a, resulting in a first electron cloud 814, a first cloud of holes 815 and a first scattered photon 810c. The first scattered photon 810c is illustrated as interacting with the detector pixel 402a in a second Compton scattering event 812b, resulting in a second electron cloud 818, a second cloud of holes 820 and a second scattered photon 810d. The second scattered photon 810d is illustrated as interacting with another detector pixel 402b in a photoelectric effect event 816, resulting in a third electron cloud 822 and a third cloud of holes 824. The subsequent photon interactions 812b, 816 may occur a number of pixels removed from the detector pixel 402a in which the first Compton scattering event 812a occurred.

Figure 2:
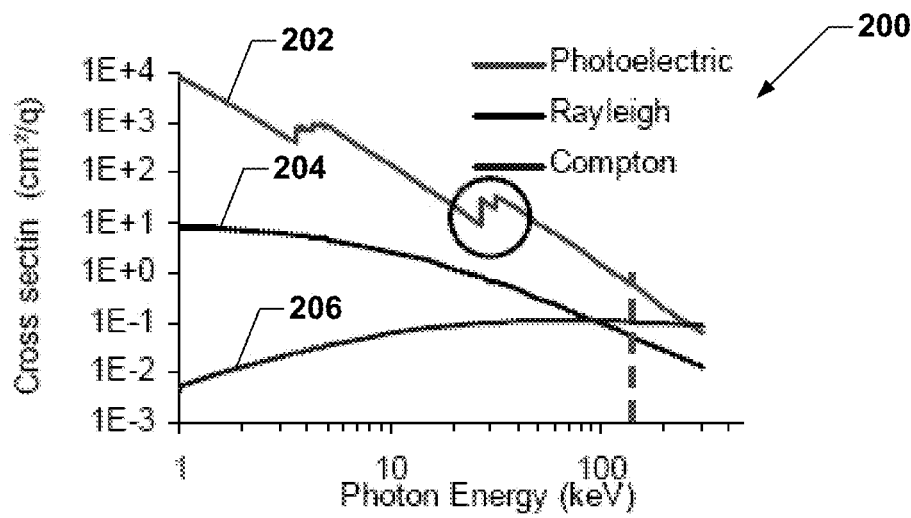
FIG. 2 is a graph of cross-sections for photoelectric, Rayleigh scattering and Compton scattering interactions in a CZT detector as a function of photon energy.

The general description of Compton scattering events presents practical issues for determining an accurate count of photon interactions per detector pixel in a CZT detector in applications such as SPECT imaging. Assuming a single energy source, such as 1-131 isotope that emits 364 keV gamma photons, FIG. 2 shows that Compton scattering dominates and is more likely than the photoelectric effect. For 364 keV photons, the maximum recoil electron energy is 214 keV and the Compton gap is 150 keV. As illustrated in FIG. 6, this means that no events should be recorded between 214 keV and 364 keV, which is the Compton gap 602. If events between 214 keV and 364 keV are present in the spectrum recorded by a detector pixel, such events are results of non-ideal detector response. However, as such a tail is continuous in nature while the Compton edge is rather abrupt, its detection may be possible in the recorded spectra.

The impact on recorded photon energy from the photoelectric and Compton scattering effects may be illustrated by examining the signal signature in the CZT readout system using 662 keV energy as an example as that is the gamma photon emitted by the readily available Cesium isotope Cs-137 used in CZT testing.

Figure 9A:
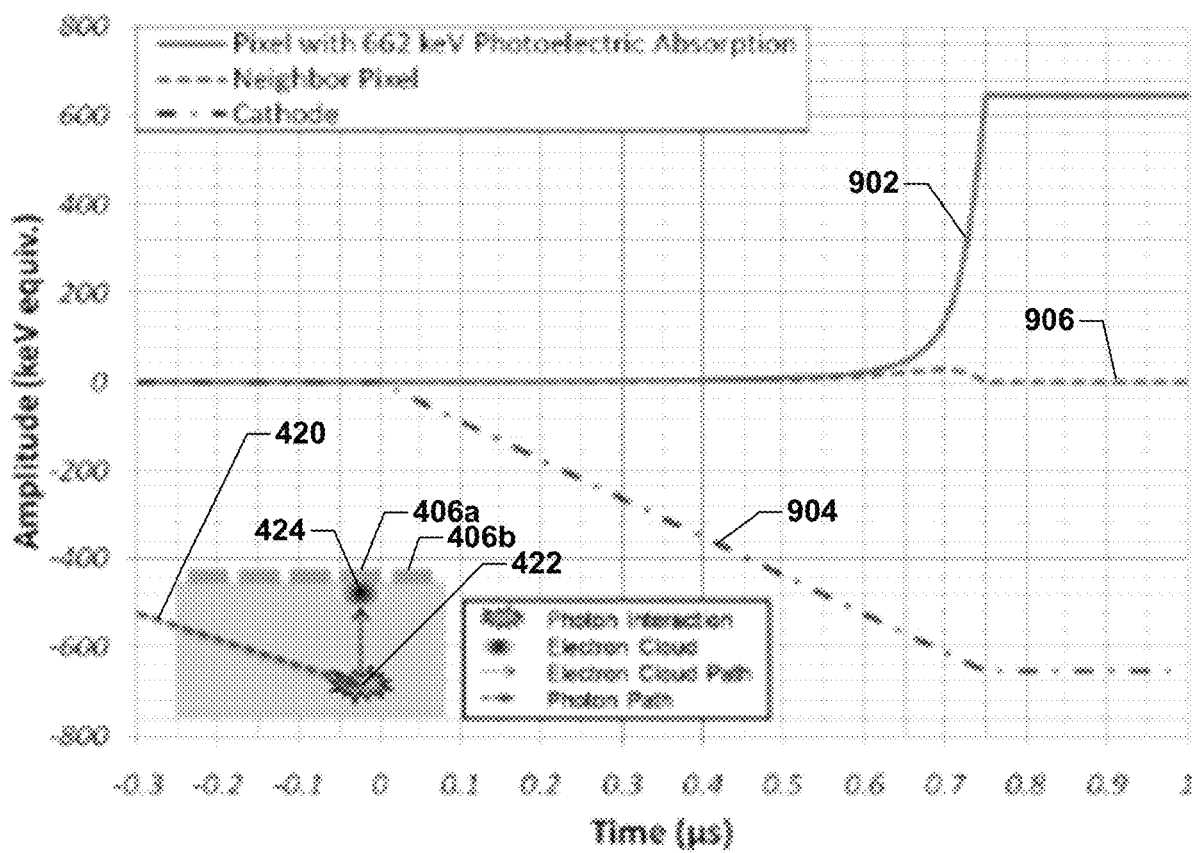
FIG. 9A is a graph and diagram showing the measured voltages in a detector pixel and an adjacent detector pixel resulting from detection of a gamma-ray photon that interacts with the detector without Compton scattering.

FIG. 9A shows an illustration of a typical single-pixel 662 keV photoelectric absorption event in a pixelated semiconductor detector, such as described with reference to FIG. 4A. FIG. 9A includes the simulated waveform responses (without noise) of the collecting detector pixel 406a in line 902, the side-neighbor detector pixel 406b in line 906, and the cathode 404 in line 904. During a photoelectric absorption interaction 422, the incident photon 420 transfers all of its energy to a bound atomic electron in the detector material. An electron cloud 424 is formed as the resulting photoelectron loses energy, ionizing atoms along its path. This electron cloud 424 is transported through the semiconductor along electric field lines toward a detector pixel anode 406a. As the electrons move, the electrons induce signals on all the detector pixel anodes 406a, 406b. In this particular interaction that occurs approximately in the center of a single pixel column, the electron cloud 424 is collected primarily on the anode 406a of that detector pixel, with only a small charge recorded on the adjoining detector pixel anode 406b. The magnitude of induction shown in lines 902 and 906 depends on the amount of charge created and the weighting potential along the charge transport track.

The cathode signal 904 has a linear slope that corresponds to the linear weighting potential of the planar cathode 404 (see FIG. 4). The rise time of the cathode signal 904 represents the cloud charge drift time in the detector.

The non-linear shape of the anode signal 902 on the detector pixel anode is due to the weighting potential of a single collecting pixel. The electron cloud drifts toward the anode 406a under the electric field induced between the anode and the cathode 404, however, a substantial amount of charge is not induced on the detector pixel 406a until the electron cloud gets near the anode. Because the illustrated interaction occurs in the center of the pixel, the waveforms of the four edge neighbor pixels and four corner neighbor pixels will be identical (illustrated by the single line 906). A small transient peak is evident in the neighbor pixel signals 906. The transient peak of the corner neighbor pixels would have a smaller amplitude than the transient peak of the corner pixels.

If the energy of the incident photon is not known, it is difficult to have a confirming signature of photoelectric absorption. A single interaction in a pixel may be a Compton scatter out of the detector. One signature of a photoelectric absorption event is the emission of a characteristic X-ray which can be emitted as the atom returns to its ground state. As described in previously, the energy of the characteristic X-ray depends on which orbital shell the photoelectron originated from as well as the elements that make up the detector crystal. Interactions with bound electrons in other shells are possible; however, they are less likely and yield lower energy X-rays. Higher energy X-rays are of primary interest here because they have a higher probability of escaping the original interaction voxel.

If a characteristic X-ray energy can be detected, the interaction can be classified as a photoelectric absorption interaction. This technique can be used to eliminate Compton continuum events in a spectrum and improve Compton sequence estimates for imaging applications by confirming the final interaction position. A photoelectric absorption event signature requires detection of a characteristic X-ray. This may be accomplished by detecting a pulse with a measured amplitude corresponding to an expected X-ray energy. If a characteristic X-ray is absorbed very close to the site of the photoelectric absorption, it cannot be distinguished from the original energy deposition and the signature is lost. This is also the case of Auger electron emission. If the characteristic X-ray is absorbed at a different depth in the same pixel as the photoelectric absorption site, then the X-ray can be distinguished based on an accurate measurement of the X-ray signal. If the characteristic X-ray is absorbed in a neighbor pixel, the amplitude of that pixel signal can be measured and compared with expected X-ray energies.

Even if a characteristic X-ray energy is measured, there is a chance that the event is actually a Compton scatter. To quantify this possibility, calculations can be made to assign a likelihood that the event is either a photoelectric absorption or a Compton scatter. This likelihood is a function of the measured energies and the interaction locations. If the position of the source is known, the incident direction of the interacting photons provides even greater accuracy in assigning a likelihood. Probabilities for potential Compton sequences can be calculated using the Compton edge test via the Compton scatter equation as well as the Klein-Nishina formula if information regarding the direction of the interacting photons is available.

Figure 9B:
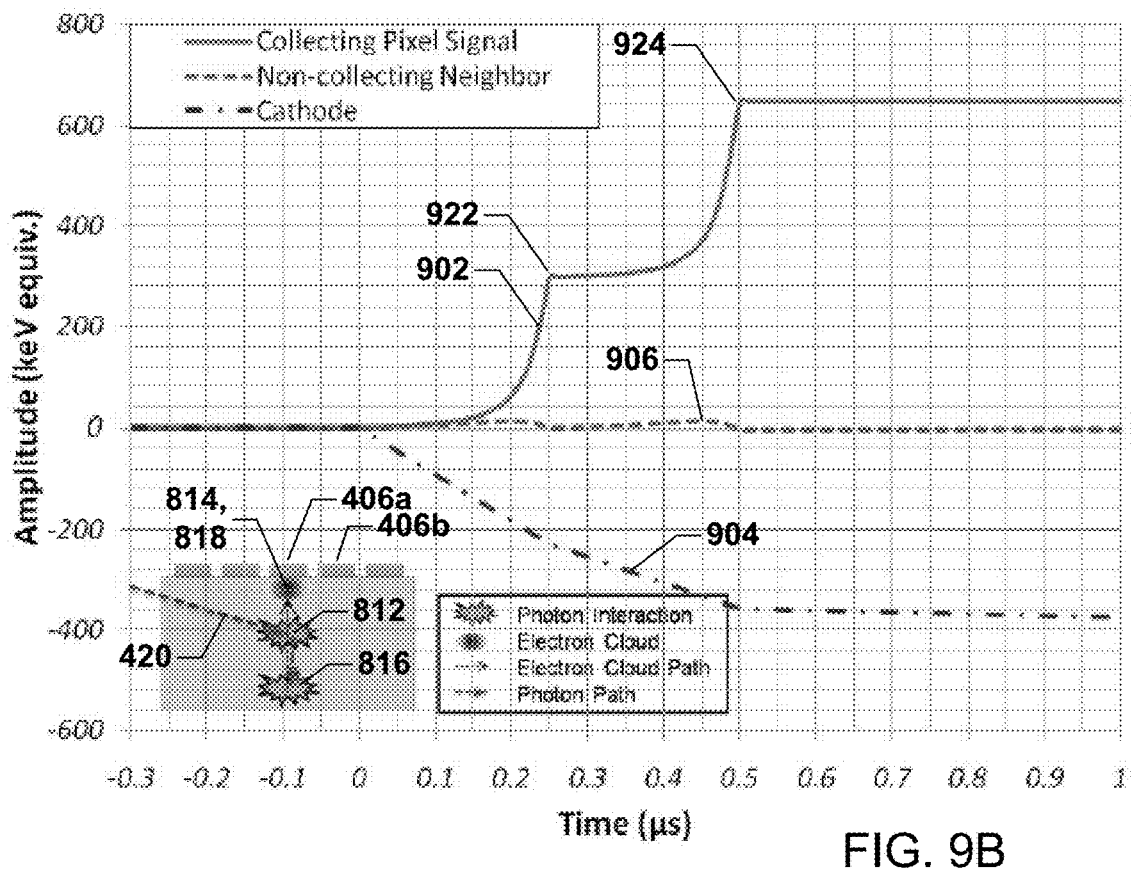
FIG. 9B is a graph and diagram showing the measured voltages in a detector pixel and an adjacent detector pixel resulting from detection of a gamma-ray photon that interacts with the detector with Compton scattering and detection of the scattered photon within the same pixel detector.

Referring to FIGS. 8B and 9B, following a Compton scatter interaction 812, which generates an associate electron cloud 814 as the recoil electron ionizes atoms as it loses energy, the scattered photon 810 may undergo a photoelectric absorption interaction 816, generating another electron cloud 818 and a corresponding number of holes 820. When more than one photon interaction occurs at different depths within a detector pixel 402a, the resulting electron clouds (e.g., 814, 818) are collected by a detector pixel (e.g., 406a) due to the finite drift speed of the electron clouds. This can be detected in the signal of the corresponding detector pixel anode 406a. FIG. 9B illustrates signals 902 that may be detected when a Compton scatter interaction 812 is followed by a photoelectric absorption interaction 816 of the scattered photon that occurs within a single detector pixel. Detection of non-coincident pixel pulses 922, 924, which results from the photon interactions at different depths, provides a signature of a Compton scatter event. Detection of a Compton scatter event as well as a signal consistent with photoelectric effect absorption of a characteristic X-ray is evidence of a complete scatter-absorption sequence in a single detector pixel as illustrated in FIG. 9B.

While not illustrated in FIGS. 8B and 9B, following an initial Compton scatter interaction 812, the scattered photon 810 may undergo another Compton scatter interaction, which also generates a recoil electron and an associate electron cloud as the recoil electron ionizes atoms as it loses energy, and the second scattered photon may undergo a photoelectric absorption interaction, generating another electron cloud, or a third Compton scattering event.

Figure 9C:
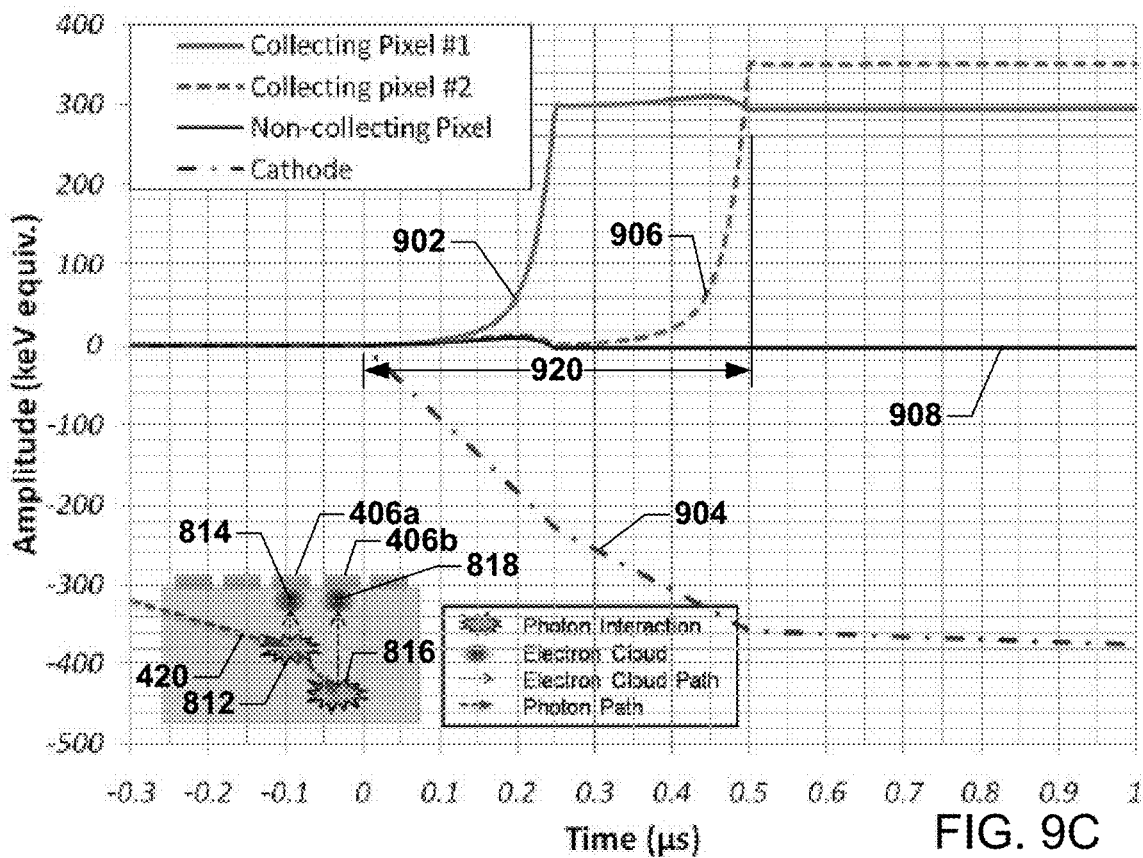
FIG. 9C is a graph and diagram showing the measured voltages in a detector pixel and an adjacent detector pixel resulting from detection of a gamma-ray photon that interacts with the detector with Compton scattering and detection of the scattered photon within the adjacent pixel detector.

If one of these non-coincident pulse energies 922, 924 corresponds to a characteristic X-ray energy, then it is possible that the scattered photon or characteristic X-ray escaped into a different detector voxel (e.g., 402b associated with anode 406b). An example of signals resulting from a Compton scatter 812 of an incident photon 420 in one detector pixel 406a (line 902) and photoelectric absorption 816 of the scattered photon or characteristic X-ray in a neighbor detector pixel 406b (line 906) is illustrated in FIG. 9C. Compton scattering of a photon in one detector pixel 406a followed by photoelectric absorption 816 in a non-neighbor detector pixel is similar, except the charge induced on each detector pixel from the other interaction (e.g., the humps shown in lines 902 and 906) would be less due to the greater distance between the interactions. As illustrated in FIG. 9C, situations in which Compton scattering of an incident photon occurs in one detector pixel (e.g., associated with anode 406a) and photoelectric effect absorption or a second Compton scattering of the scattered photon or characteristic X-ray occurs in an adjacent or nonadjacent detector pixel is characterized by charge signals being measured by two different detector pixel anodes within a very short time window, such within less than 0.5 microseconds of each other.

Figure 9D:
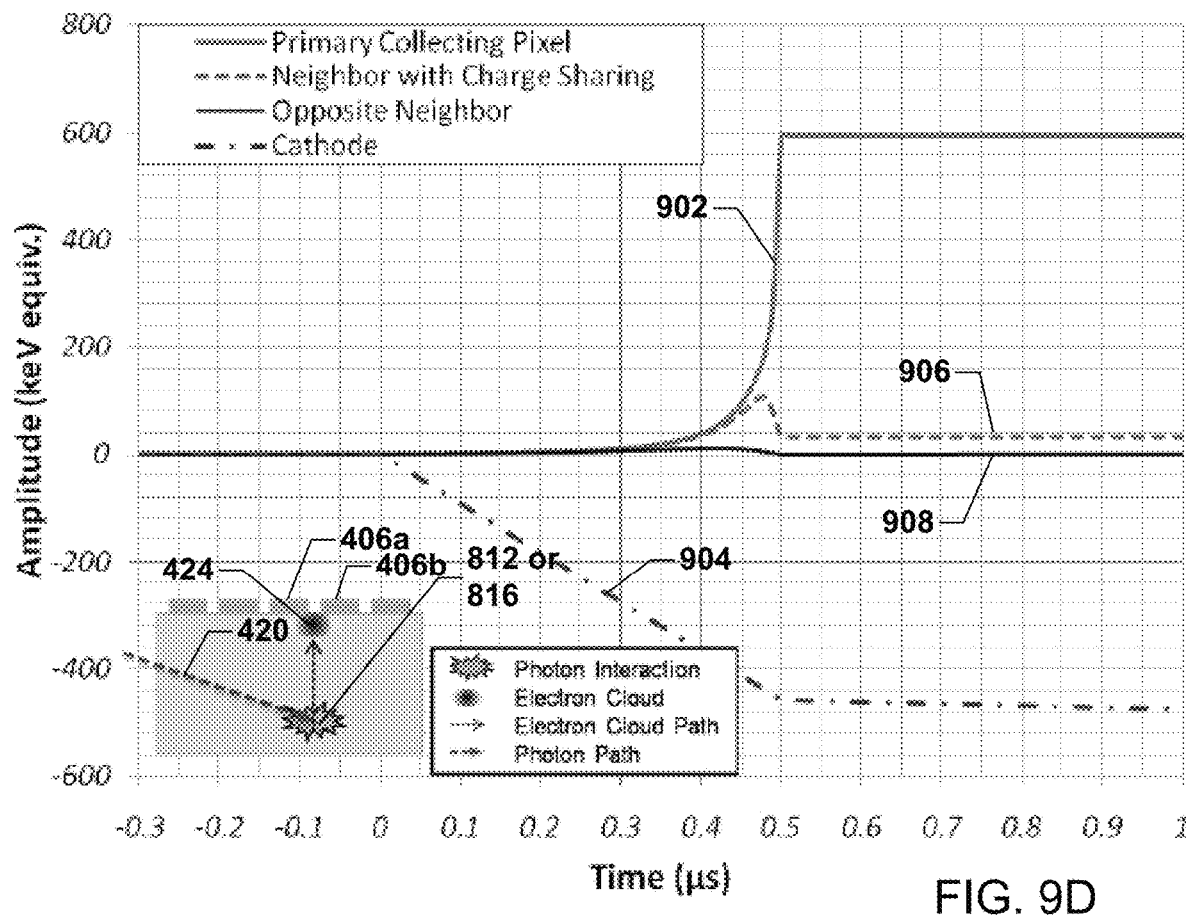
FIG. 9D is a graph and diagram showing the measured voltages in adjacent detector pixels resulting from detection of a gamma-ray photon that interacts with the detector without Compton scattering but measurement of the electron cloud in the adjacent pixel detectors.

To add complexity of photon interaction signatures, Compton scattering and photoelectron absorption events may occur near the boundary of a detector pixel or within the gap between detector pixels as illustrated in FIG. 9D. In such circumstances, the electron cloud 424 resulting from a Compton scatter interaction 812 or a photoelectric absorption interaction 816 follows electric field lines near the gap 410 between detector pixels, resulting in fractions (426a, 426b) of the electron cloud 424 being shared between the two (or more) detector pixel anodes 406a, 406b. The magnitude and characteristics of this phenomenon depend on the detector pixel dimensions, spacing, and presence of a steering grid. The likelihood of such charge sharing increases with the electron cloud size, which is a function of the energy deposited by the interaction. As illustrated in FIG. 9D, when Compton scattering and photoelectron absorption events occurs near the boundary of a detector pixel or within the gap between detector pixels, a fraction of the electron cloud is collected by two (or more) different pixel anodes 406a, 406b, resulting in the signals 902 and 906. Such a waveform set provides evidence that charge was collected in two detector pixels. The non-collecting opposite neighbor signal 908 may also include a smaller transient signal 908 formed by charge induction from the electron cloud fraction collected by the center detector pixel.

The signature of a charge sharing event is near-coincident collection of charge on two neighboring pixels with an observable transient peak. It is possible that a charge sharing event will not have exhibit transient if the charge shared is greater than the induced transient height. It is also possible that a same-depth Compton scatter into a neighbor produces a set of waveforms identical to that of a charge sharing event. Such a same-depth Compton scatter is relatively rare and can be treated using the formalism discussed for characteristic X-rays. Calculations of the sub-pixel interaction position also provide information concerning charge sharing classification. If the result of the position estimate shows that there are two separate charge clouds in two separate pixels, then Compton scattering, or another multiple-particle event has occurred.

FIG. 9C also illustrates that the time between a photon-detector interaction and complete collection of the resulting electron cloud(s), which is driven by the time it takes the resulting electron cloud to reach the detector pixel anode, is on the order of a few tenths of a microsecond (e.g., ≤0.5 μs). Thus, the signal characteristics of one or more Compton scattering events and a photoelectric absorption event resulting from a single incident photon can be captured within a brief sampling window, referred to as an "event frame" 920. Accordingly, in various embodiments the spectroscopic Application Specific Circuit (ASIC) receiving and processing signals from detector pixels may be configured to recognize and treat detection events that occur within event frames of a few tenths of a microsecond as related to single photon detections, subject to some counting criterial described below. Thus, the term "event frame" 920 refers to a brief duration of time (e.g., ≤0.5 μs) used by detector circuitry to recognize single photon detection events that produce multiple signals, either in a single detector pixel or in two or more detector pixels. In low count rate applications, such as SPECT imaging in which a small amount of radionuclide is used to reduce the risk to imaging subjects, the probability of two incident gamma ray photons interacting with a limited region of the detector (e.g., within a diameter of 20 detector pixels) within such a brief event frame is low, thus enabling two or more events detected within an event frame 920, such as illustrated in FIGS. 8C and 9C to be treated as resulting from a single incident photon.

In various embodiments, event classification algorithms using noiseless simulated waveforms are used to determine the nature of the photon interactions with one or more detector pixels. If the magnitude of full energy depositions and interaction locations are known exactly, as is the case for many isotopes used in SPECT imaging, the uncertainty remains only when detector signatures overlap or there is insufficient information.

There are several detector response complications that affect the uncertainty of an detection event classification algorithm. The inherent energy uncertainty limits the accuracy and efficiency of any detection system. Charge generation statistics, material non-uniformity, front-end electronic noise, and leakage current all affect the final measurable quantity of the original energy deposition. Depth dependent pulse height is another detector-specific response complication. Because only the electron signal component is used (single polarity charge sensing), same-energy interactions at different depths result in different pulse heights. Electron trapping and weighting potential contribute to this non-uniformity. Since the depth within a detector pixel of a photon interaction cannot be calculated event-by event, this phenomenon cannot be corrected.

A commercially available spectroscopic ASIC that may be used with a VERITON module SPECT imager has charge-coincidence detection capability, namely the spectroscopic ASIC sends a signal when two neighboring detector pixels detect events within a current readout frame (i.e., approximately simultaneously). However, such a spectroscopic ASIC does not provide depth-of-interaction (DOI) discrimination capability. As a result, various embodiments classify the detected events in the VERITON module as described for the following cases.

Case A—Single event of energy $E_0$—The module has no way of telling whether as single event is a photoelectric absorption event, one of two (or more) Compton scattering events, or one of a charge-shared event (the other being not detectable). Consequently, photoelectric absorption is assumed for such events, because this interaction is much more likely (even when Compton scattering dominates only some fraction of those events result in single photon absorption). For $E_0$ corresponding to the Compton gap (see FIG. 6) there is a certainty that the event is truly a photoelectric absorption event although due to finite energy resolution of the system the width of the Compton gap needs to be reduced by ER value on both ends. For energies below the Compton gap the assignment does not matter as these events will be assigned to the tail. For example, for Tc99m the photon between 100 keV and 140 keV cannot be Compton (see FIG. 7) so it is a photoelectric absorption event, while for energies below 100 keV it can be either a photoelectric absorption event or a Compton scatter interaction. However, it doesn't really matter in SPECT imaging as the detection is assigned to the Tc99m tail, which is outside counting window.

Case B—Two events E1 and E2 in the same location—In this case, two events are detected within one readout frame and are physically located in the same detector pixel. In the event of this detected signal, it is assumed a Compton scattering sequence has occurred and the measured energies are added. The readout system will almost always read the total energy as E1+E2 so distinguishing between Compton scattering and a photoelectric absorption event in the second event is not possible and really not needed. In practice case B is treated the same as case A.

Case C—Two neighboring events E1 and E2—In this case, two events are detected within one readout frame by neighboring detector pixels (north-south, east-west but not diagonal). In the event of this detected signal, a charge-shared event is assumed and the detected energies of both events are added (i.e., E1+E2). In rare cases this is the wrong assumption as two independent photons can be detected simultaneously but due to low count rate in SPECT imaging this would be rare. The events E1 and E2 can be also part of a Compton scattering sequence, but even in that case adding both energies is correct. Only in some rare cases will a Compton scattering sequence involve more than two photons such that adding will not result in a measure of the complete primary photon energy. This also to applies to charge-sharing where 3-pixel and 4-pixel splits are possible.

CASE D—Two non-neighboring events E1 and E2—In this case, two events are detected within one readout frame two detector pixels that are not neighbors. In the event of this detected signal, it is assumed that the signals are the result of a Compton scattering sequence event and the detected energies of both events are added and assigned to the detector pixel that measure the larger energy as that energy is more likely to correspond to the location of the primary photon entry. In rare cases this is the wrong assumption as two independent photons can be detected simultaneously but due to low count rate in SPECT this would be rare. The location (i.e., the detector pixel) of events E1 and E2 can also be checked again distance between the two detector pixels—there is a significant probability of this event happening between detector pixels that are separated by 2-5 pixels, the probability of this event happening between detector pixels that are separated by 10-20 pixels is very small. Statistical calculations can be performed and coded in some embodiments depending on the detector pixel size, sensor thickness and photon energy of interest to indicate how many pixels away it is reasonable to expect E1 and E2 to result from one Compton sequence, and thus be treated as one event with the measured energies added.

To summarize, in a pixelated detector there can be four different cases or scenarios of photon detection. Case A is a standard photo-electric absorption event that is usually the most frequent event. Case B is rare and results in the same classification and localization of the event as Case A. Case C is addressed by a standard charge-sharing correction, particularly if a sub-pixelization scheme is used. Case D is a new Compton correction, statistically more likely to happen than case B, so efficiency gains can be substantial. The probabilities of cases A, B, C, D may be assessed for 7.3 mm thickness, 1.23 mm pixel pitch and 364 keV photon energy. Other potential SPECT and XRD spectroscopic systems may use even smaller detector pixel pitches, in which case Compton corrections may be even more important.

Figure 10A:
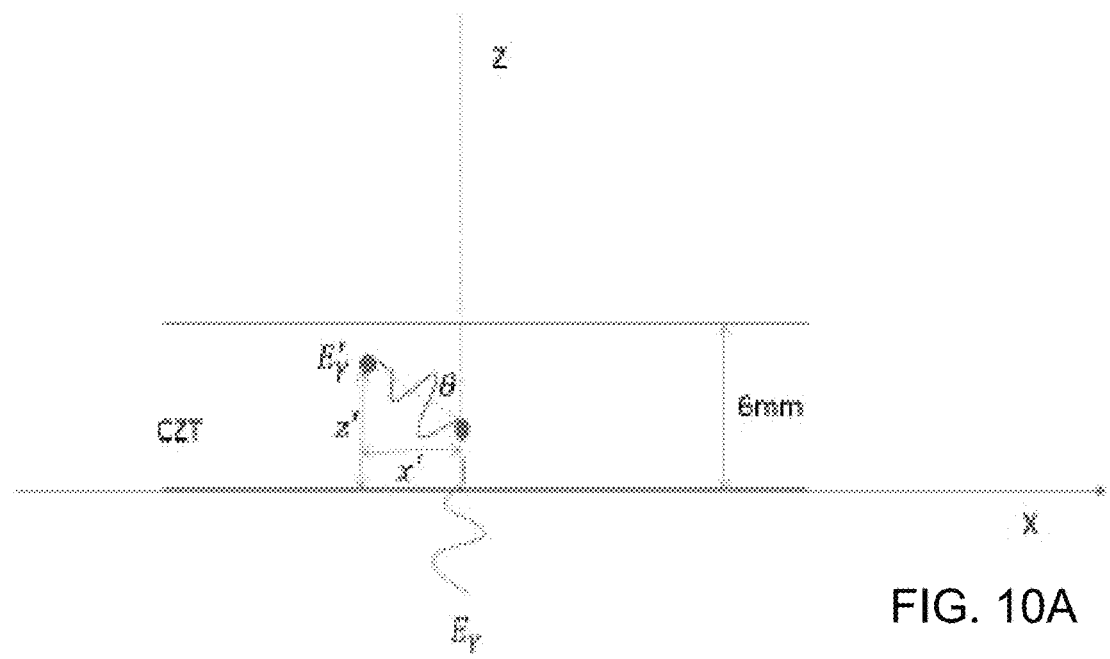
FIG. 10A is a conceptual diagram illustrating a model for conducting Monte-Carlo analysis if Compton scattering of a gamma-ray within a 6 mm thick CZT radiation detector.
Figure 10B:
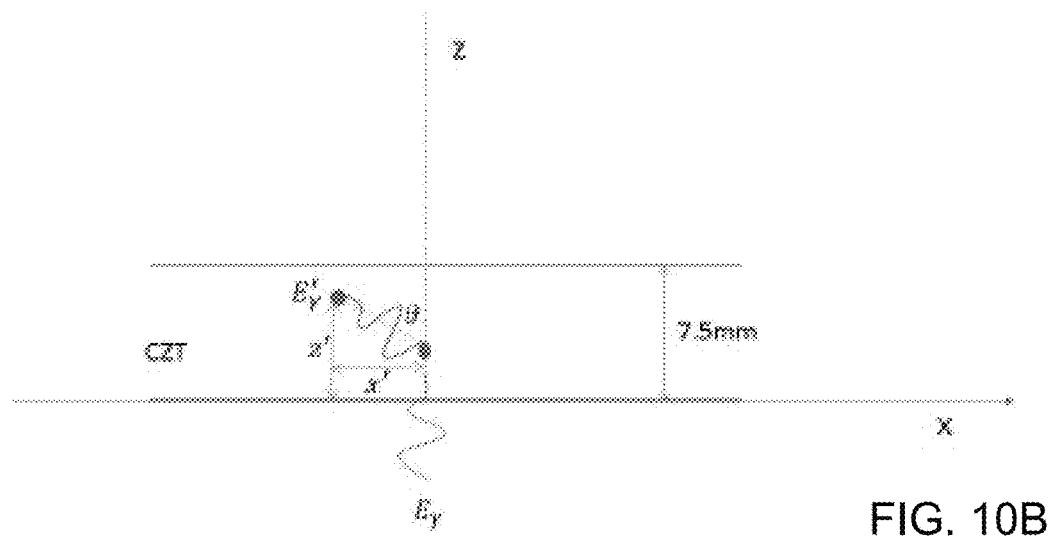
FIG. 10B is a conceptual diagram illustrating a model for conducting Monte-Carlo analysis of Compton scattering of a gamma-ray within a 7.5 mm thick CZT radiation detector.

To illustrate how much efficiency can be gained by employing Compton scattering corrections of various embodiments, Monte-Carlo (MC) simulations have been performed using a simple 2D geometry illustrated in FIGS. 10A and 10B. Two extreme cases have been considered: a 6 mm thick CZT detector detecting 122 keV gamma rays emitted by Co-57, and a 7.5 mm thick CZT detector detecting 363 keV gamma rays emitted by I-131. The main results of the simulations is illustrated in FIGS. 11A and 11B.

Figure 11A:
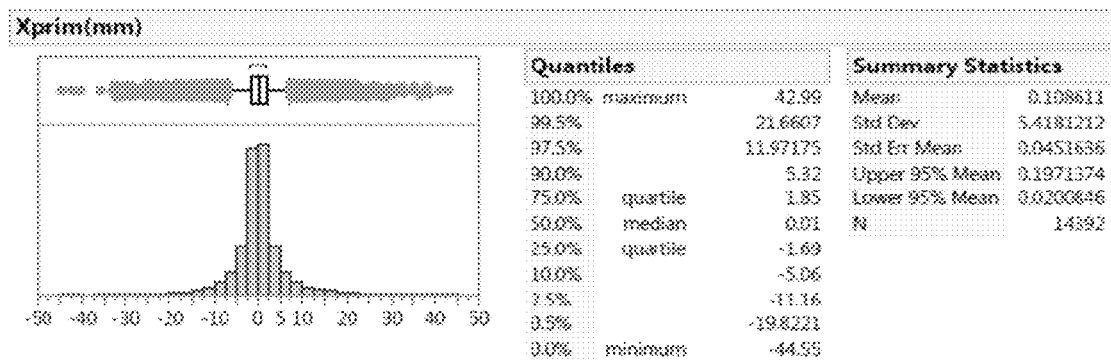
FIGS. 11A and 11B are a graph and table of photon detection events vs distance from a first photon interaction based on Monte-Carlo simulation analyses of the models illustrated in FIGS. 10A and 10B.
Figure 11B:
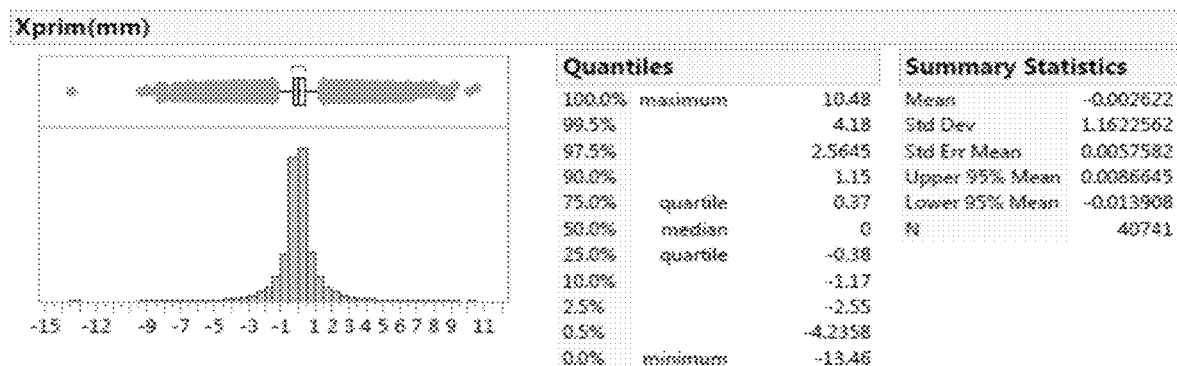

In the first case of Co-57 gamma rays detected by a 6 mm thick detector, most Compton scattered photons (90%) undergo a photoelectric absorption event within 1.15 mm, as illustrated in FIG. 11A. This means that with a detector pixel pitch of 1.23 mm, the Compton scattering and photoelectric absorption events are confined to the same detector pixel, hence a Compton scattering correction is not needed as expected. Even, if the pitch is 0.5 mm, most of the Compton scattered photons would undergo photoelectric absorption one pixel away, hence a routine charge-sharing correction would take care of these Compton effects.

A dramatically different situation exists in the second case of I-131 (363 keV) gamma rays interacting with a 7.5 mm thick detector. In this case, the lateral spread of Compton scattered photons reaches 5 mm for 90% of the photons, as shown in FIG. 11A. This means that with a detector pixel pitch of 1.23 mm, Compton scattered photons are likely to be detected up to 4 pixels away from the first Compton scattering event. Thus, a Compton scattering correction is may be used for 76 (9×9-5) pixels. If the detector pitch is 0.5 mm, most of the detector pixels in the sensor would have to be corrected as the reach of 90% of Compton scattered photons is up to 10 pixels away from the detector pixel where the first Compton scattering of an incident photon occurred.

Various embodiments include methods for applying corrections for Compton scattering of photons in SPECT imaging systems.

Figure 12A:
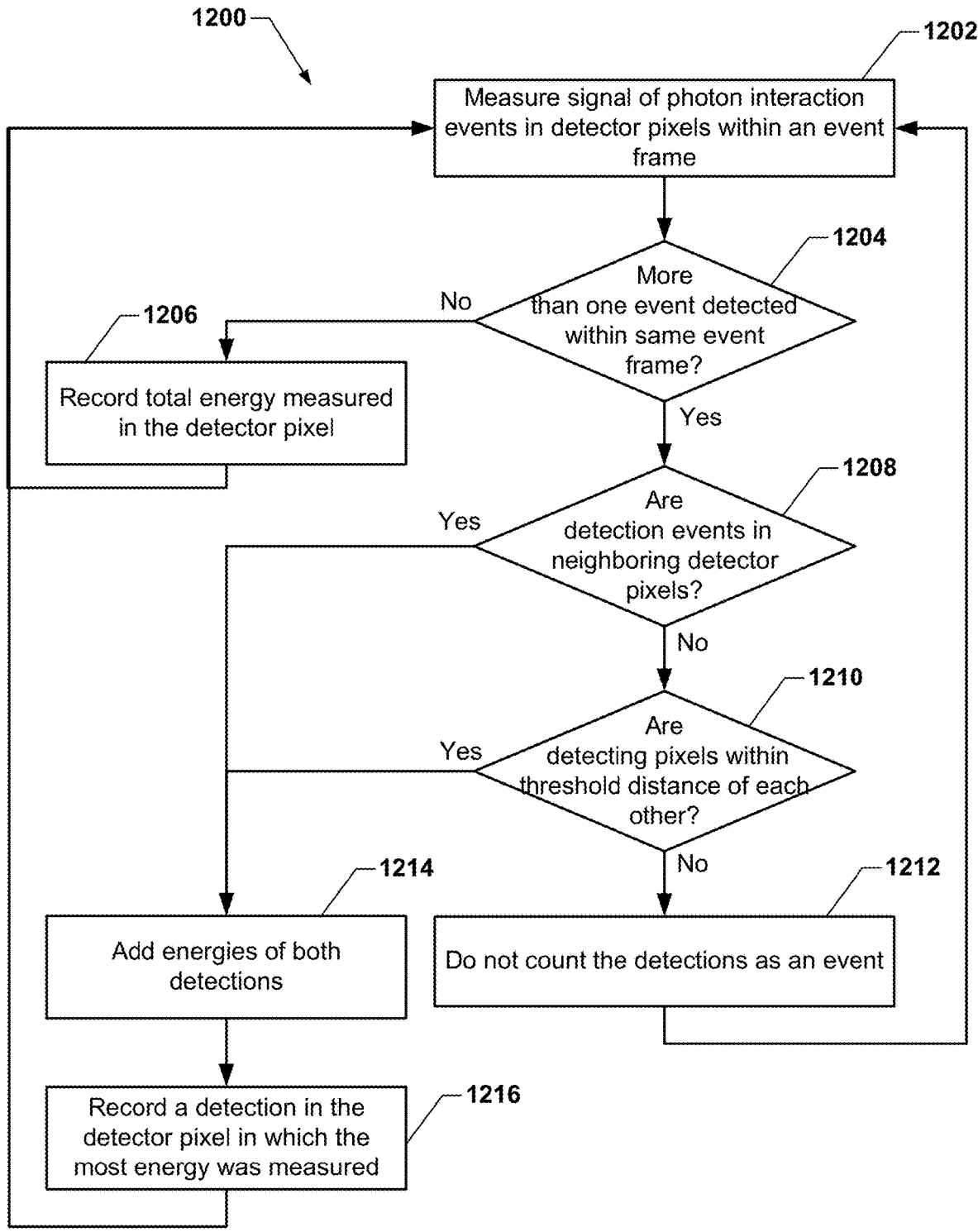
FIGS. 12A and 12B are process flow diagrams illustrating methods of compensating for charge share affects in pixel radiation detectors according to various embodiments.

FIG. 12A illustrates an embodiment method 1200 for measuring and recording radiation detection events suitable for SPECT imaging using a pixelated radiation detector comprising a plurality of detector pixels. The method 1200 may be implemented within a processor of a SPECT imaging system, such as the correction and multi-channel analyzer unit 112, which may include an ASIC capable of detecting two or more detection events in separate detector pixels within an event frame of a particular duration. Some of the operations may be performed in a digital image processing computer 114.

In block 1202, the processor may measure the signal of photon interactions events within detector pixels during an event frame.

In determination block 1204, the processor may determine whether more than one event was detected in multiple detector pixels within the event frame.

In response to determining that only a single event or multiple events within a single detector pixel was detected during the event frame (i.e., determination block 1204="No"), the processor may record the event as a single photon detection by the detector pixel recording the total energy measured in the event in block 1206.

In response to determining that multiple events in multiple detector pixels were detected during the event frame (i.e., determination block 1204="Yes"), the processor may determine whether the multiple events were measured in neighboring detector pixels in determination block 1208.

In response to determining that the multiple events were not detected in neighboring detector pixels (i.e., determination block 1208="No"), the processor may determine whether the detecting pixels are within a threshold distance of each other in determination block 1210. The threshold distance may be determined in advance based upon the energy and flux of the gamma ray photons used in the imaging session and characteristics of the detector pixels, including detector materials, detector thickness, detector pixel size, separation distance between detector pixels, etc. The threshold distance may be a distance within which it is more likely that a Compton scattering sequence of events has occurred than multiple independent photon interactions have been detected nearly simultaneously. In a low count rate imaging application, such as SPECT imaging, detection of multiple independent photon interactions within the event frame will occur relatively infrequently (i.e., with a low probability). Therefore, the threshold distance may be the distance (e.g., in number of detector pixels) within which ninety percent (90%) of Compton scattered photons may travel in the detector materials before another Compton scattering event or absorption via the photoelectric effect. Beyond that distance, the likelihood that the two nearly simultaneous detection events resulted from the Compton scattering of a single incident photon is less than the probability that the two detection events of the result of two independent incident photons. For example, for a SPECT imaging session with a 7.5 mm thick detector featuring a detector pixel pitch of 1.23 mm and using I-131 as the source of 363 keV gamma rays, the threshold distance may be set at four pixels.

In response to determining that the detecting pixels are not within the threshold distance of each (i.e., determination block 1210="No"), the processor may ignore or not count the signals as a single detection event in block 1212.

In response to determining that the multiple events were detected in neighboring detector pixels (i.e., determination block 1208="Yes"), or in response to determining that the detecting pixels are within the threshold distance of each (i.e., determination block 1210="Yes"), the processor may add the energies of the two detection events in block 1214 and record the detection location of the event as the detector pixel in which the most energy was measured in block 1216. Thus, when two events are detected in neighboring pixels or within two pixels within a threshold distance of one another their respective energies (E1 and E2) are added and the sum of their energies is allocated to the detector pixel measuring the higher energy. Whether this represents charge-sharing or Compton sequence that doesn't matter. Further, when two events are not in neighboring pixels their energies (E1 and E2) are added only if the probability of a Compton scattering sequence (that probability determined based on pixel pitch, photon energy, etc.) is greater than the probability of two separate individual photons being detected.

The processors of the method 1200 may continue continuously, being repeated for each event frame during the imaging session.

Figure 12B:
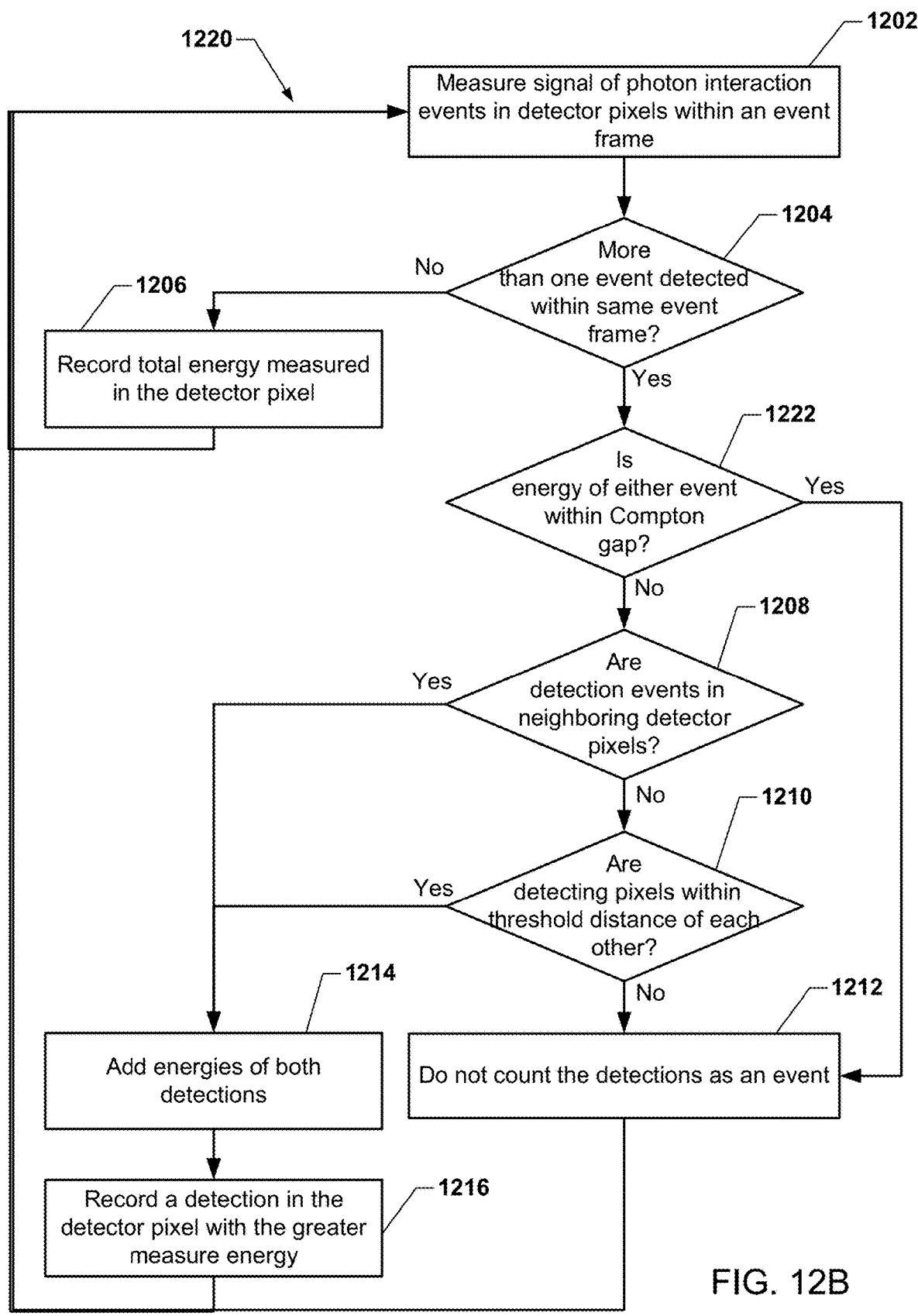

FIG. 12B illustrates a further method 1220 according to another embodiment that takes into consideration the Compton gap when counting of multiple events as a single Compton scattering sequence. The method 1220 may be implemented within a processor of a SPECT imaging system, such as the correction and multi-channel analyzer unit 112, which may include an ASIC capable of detecting two or more detection events in separate detector pixels within an event frame of a particular duration. Some of the operations may be performed in a digital image processing computer 114. In the method 1220, the operations of blocks 1202-1216 of the method 1200 may be performed as described with reference to FIG. 12A with the exception of testing whether any detected events fall within the Compton gap.

Specifically, in response to determining that more than one event was detected within the same event frame (i.e., determination block 1204="Yes"), the processor may determine whether the measured energy of either event was within the Compton gap in determination block 1202. The Compton gap can be calculated prior to the measurements based upon the primary photon energy. For example, if the source of Gamma ray photons is I-131, which have a primary photon energy of 364 keV, the Compton gap is 150 keV and the Compton edge is at 214 keV (364 keV-150 keV=214 keV). Assuming an energy resolution of 10 keV, this means that there should be no Compton scattered photons between 204 keV and 354 keV. Any photon detected in that range is therefore not the result of a Compton event. Applying this condition will help in proper classification of the Compton event.

In response to determining that the measured energy of either event was within the Compton gap (i.e., determination block 1222="Yes"), the processor may ignore or not count the two or more near simultaneous signals as a single detection event in block 1212. Otherwise, in response to determining that the measured energy of the detected events falls outside the Compton (i.e., determination block 1222="No"), the processor may perform the operations in determination block 1208 as described with reference to FIG. 12A.

Figure 13:
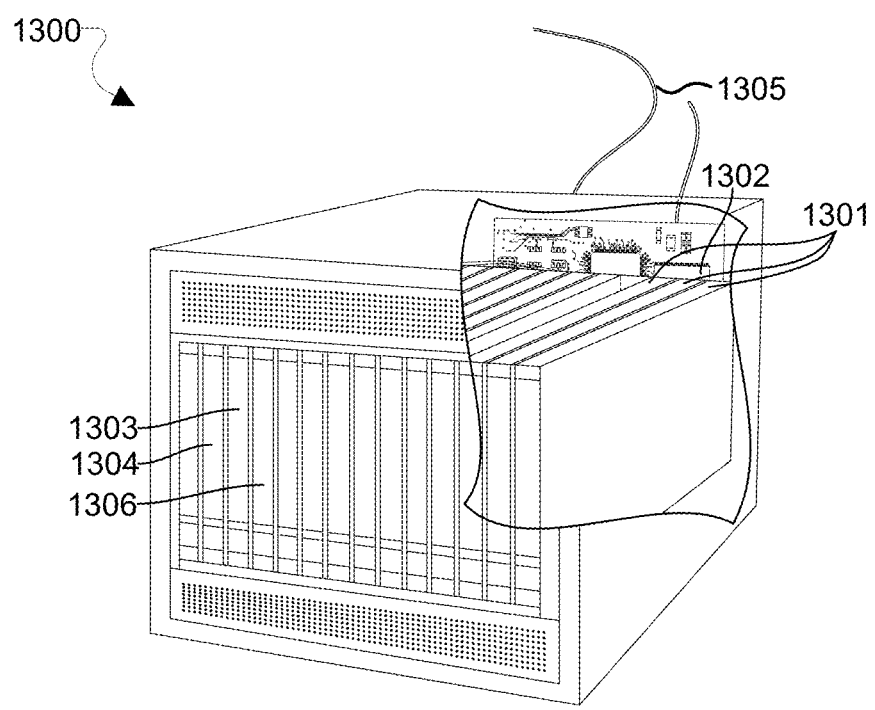
FIG. 13 is a component block diagram illustrating an example server suitable for use with the various embodiments.

The various embodiments (including, but not limited to, embodiments described above with reference to FIGS. 12A and 12B) may be implemented in computing systems, such as any of a variety of commercially available computers 1300 as illustrated in FIG. 13. Such a computer 1300 typically includes one or more processors 1301 coupled to volatile memory 1302 and a large capacity nonvolatile memory, such as a disk drive 1304. As illustrated in FIG. 13, one or more processors 1301 may be added to the computer 1300 by inserting them into the racks of the assembly. The computer 1300 may also include a floppy disc drive, compact disc (CD) or digital versatile disc (DVD) disc drive 1306 coupled to the one or more processors 1301. The computer 1300 may also include network access ports 1303 coupled to the one or more processors 1301 for establishing network interface connections with a network 1305, such as a local area network coupled to other computers and servers, or the Internet.

The present embodiments may be implemented in systems used for medical imaging, Single Photon Emission Computed Tomography (SPECT) for medical applications, and for non-medical imaging applications, such as in baggage security scanning and industrial inspection applications.

Compton scattering effects in pixel radiation detectors may cause efficiency variations for the reasons explained above. The various embodiments overcome some issues caused by Compton scattering effects in pixel radiation detectors by providing a method that enables counting certain multiple detection events as a single photon detection. The methods of various embodiments apply in particular to spectroscopic applications, and for systems that use small-pixel detectors in SPECT. In particular, various embodiments include determining whether gamma ray detection events occurred in two or more detector pixels within an event frame; determining whether the detection events occurred in detector pixels within a threshold distance of each other in response to determining that detection events occurred in two or more detector pixels within the event frame; and recording the two or more detection events as a single detection event having an energy equal to the sum of the measured energies of the two or more detection events located in the detector pixel having a highest measured energy in response to determining that the detection events occurred in detector pixels within the threshold distance of each other. Some embodiments may further include ignoring or not recording the two or more detection events in response to determining that the detection events occurred in detector pixels separated by more than the threshold distance. In some embodiments, the threshold distance is predetermined based upon an energy of gamma ray photons incident on the detector and a characteristic of pixel detectors in the detector. A characteristic of pixel detectors in the detector used in determining the threshold distance may include one or more of detector materials, detector thickness, detector pixel size, or separation distance between detector pixels. The threshold distance may be predetermined as a distance, which may be predetermined terms of a number of detector pixels, within which a predetermined fraction of Compton scattered photons may travel in the detector materials before another Compton scattering event or absorption via the photoelectric effect. In some embodiments, the threshold distance may be set at a distance within which a majority of Compton scattered photons will undergo another interaction with a detector pixel. In some embodiments, the threshold distance may be set at a distance within which a statistically significant number of Compton scattered photons will undergo another interaction with a detector pixel, such as one standard deviation ($\sigma$) or 86%, two $\sigma$ or 98%, three $\sigma$ or 99.9%. In some embodiments, the threshold distance may be set at a distance within which another percentage of Compton scattered photons will undergo another interaction with a detector pixel, such as 85%, 90%, 95%, etc. Some embodiments may further include determining whether an energy measured in any of the two or more detector pixels is within a Compton gap of gamma ray photons incident on the detector; and ignoring or not recording the two or more detection events in response to determining that the energy measured in any of the two or more detector pixels is within the Compton gap of gamma ray photons incident on the detector.

Computer program code or executable instructions for execution on a programmable processor for carrying out operations of the various embodiments may be written in a high level programming language such as C, C++, C #, Smalltalk, Java, JavaScript, Visual Basic, a Structured Query Language (e.g., Transact-SQL), Perl, or in various other programming languages. Embodiments may be implemented as program code or processor-executable instructions stored on a non-transitory processor-readable storage medium that are configured to cause a processor coupled to a pixelated radiation detector, such as a processor or analysis unit of a SPECT imaging system, to perform operations of any of the various embodiments. Program code or processor-executable instructions stored on a non-transitory processor readable storage medium as used in this application may refer to machine language code (such as object code) whose format is understandable by a processor. Non-transitory processor-readable storage medium include any form of media used for storing program code or processor-executable instructions including, for example, RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a processor or computer.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. A method of correcting for Compton scattering effects in a pixel radiation detector capable of registering gamma ray detection events occurring in two or more detector pixels within an event frame, comprising:
   determining whether gamma ray detection events occurred in two or more detector pixels within an event frame;
   in response to determining that the gamma ray detection events occurred in the two or more detector pixels within the event frame, determining whether the gamma ray detection events that occurred in the two or more detector pixels within the event frame occurred in the two or more detector pixels within a threshold distance of each other; and
   recording the gamma ray detection events, which occurred in the two or more detector pixels within the event frame as a single gamma ray detection event having an energy equal to a sum of measured energies of the gamma ray detection events, which occurred in the two or more detector pixels within the event frame and in a location of a detector pixel of the two or more detector pixels having a highest measured energy in response to determining that the gamma ray detection events occurred in the two or more detector pixels within the threshold distance of each other.

2. The method of claim 1, further comprising:
   ignoring or not recording the gamma ray detection events, which occurred in the two or more detector pixels in response to determining that the gamma ray detection events occurred in the two or more detector pixels separated by more than the threshold distance.

3. The method of claim 1, wherein the threshold distance is a predetermined threshold distance that is based upon an energy of gamma ray photons incident on the pixel radiation detector and a characteristic of the two or more detector pixels in the pixel radiation detector.

4. The method of claim 3, wherein the characteristic of the two or more detector pixels in the pixel radiation detector upon which the predetermined threshold distance is based includes one or more of detector materials, a detector thickness, a detector pixel size, or a separation distance between detector pixels.

5. The method of claim 3, wherein the threshold distance is a predetermined threshold distance within which a predefined fraction of Compton scattered photons will undergo another Compton scattering event or an absorption via a photoelectric effect.

6. The method of claim 5, wherein the predetermined threshold distance is defined in terms of a number of detector pixels.

7. The method of claim 1, further comprising:
   determining whether an energy measured in any of the two or more detector pixels is within a Compton gap of gamma ray photons incident on the pixel radiation detector; and
   ignoring or not recording the gamma ray detection events, which occurred in the two or more detector pixels in response to determining that the energy measured in any of the two or more detector pixels is within the Compton gap of gamma ray photons incident on the pixel radiation detector.

8. A Single Photon Emission Computed Tomography (SPECT) imaging system, comprising:
   a pixel radiation detector including detector pixels; and
   an analyzer unit configured to receive data from the detector pixels and output analyzed data, wherein the analyzer unit is configured to perform operations of:
      determining whether gamma ray detection events occurred in two or more detector pixels within an event frame;
      in response to determining that the gamma ray detection events occurred in the two or more detector pixels within the event frame, determining whether the gamma ray detection events that occurred in the two or more detector pixels within the event frame occurred in the two or more detector pixels within a threshold distance of each other; and
      recording the gamma ray detection events, which occurred in the two or more detector pixels within the event frame as a single gamma ray detection event having an energy equal to a sum of measured energies of the gamma ray detection events, which occurred in the two or more detector pixels within the event frame and in a location of a detector pixel of the two or more detector pixels having a highest measured energy in response to determining that the gamma ray detection events occurred in the two or more detector pixels within the threshold distance of each other.

9. The SPECT imaging system of claim 8, wherein the analyzer unit is further configured to perform operations of ignoring or not recording the gamma ray detection events, which occurred in the two or more detector pixels in response to determining that the gamma ray detection events occurred in the two or more detector pixels separated by more than the threshold distance.

10. The SPECT imaging system of claim 8, wherein the threshold distance is a predetermined threshold distance that is based upon an energy of gamma ray photons incident on the pixel radiation detector and a characteristic of the two or more detector pixels in the pixel radiation detector.

11. The SPECT imaging system of claim 10, wherein the characteristic of the two or more detector pixels in the pixel radiation detector upon which the predetermined threshold distance is based includes one or more of detector materials, a detector thickness, a detector pixel size, or a separation distance between detector pixels.

12. The SPECT imaging system of claim 11, wherein the threshold distance is a predetermined threshold distance within which a predefined fraction of Compton scattered photons will undergo another Compton scattering event or an absorption via a photoelectric effect.

13. The SPECT imaging system of claim 12, wherein the predetermined threshold distance is defined in terms of a number of detector pixels.

14. The SPECT imaging system of claim 8, wherein the analyzer unit is configured to perform operations further comprising:
   determining whether an energy measured in any of the two or more detector pixels is within a Compton gap of gamma ray photons incident on the pixel radiation detector; and
   ignoring or not recording the gamma ray detection events, which occurred in the two or more detector pixels in response to determining that the energy measured in any of the two or more detector pixels is within the Compton gap of gamma ray photons incident on the pixel radiation detector.

15. A non-transitory processor-readable medium having stored thereon processor-executable instructions configured to cause a processor of a pixel radiation detector capable of registering gamma ray detection events occurring in two or more detector pixels within an event frame to perform operations comprising:
- determining whether gamma ray detection events occurred in two or more detector pixels within an event frame;
- in response to determining that the gamma ray detection events occurred in the two or more detector pixels within the event frame, determining whether the gamma ray detection events that occurred in the two or more detector pixels within the event frame occurred in the two or more detector pixels within a threshold distance of each other; and
- recording the gamma ray detection events, which occurred in the two or more detector pixels within the event frame as a single gamma ray detection event having an energy equal to a sum of measured energies of the gamma ray detection events, which occurred in the two or more detector pixels within the event frame and in a location of a detector pixel of the two or more detector pixels having a highest measured energy in response to determining that the gamma ray detection events occurred in the two or more detector pixels within the threshold distance of each other.

16. The non-transitory processor-readable medium of claim 15, wherein the stored processor-executable instructions are configured to cause the processor to perform operations further comprising:
- ignoring or not recording the gamma ray detection events, which occurred in the two or more detector pixels in response to determining that the gamma ray detection events occurred in the two or more detector pixels separated by more than the threshold distance.

17. The non-transitory processor-readable medium of claim 15, wherein the threshold distance is a predetermined threshold distance that is based upon an energy of gamma ray photons incident on the pixel radiation detector and a characteristic of the two or more detector pixels in the pixel radiation detector.

18. The non-transitory processor-readable medium of claim 17, wherein the characteristic of the two or more detector pixels in the pixel radiation detector upon which the threshold distance is based includes one or more of detector materials, a detector thickness, a detector pixel size, or a separation distance between detector pixels.

19. The non-transitory processor-readable medium of claim 17, wherein the threshold distance is a predetermined threshold distance within which ninety percent (90%) of Compton scattered photons may travel in detector materials before another Compton scattering event or an absorption via a photoelectric effect.

20. The non-transitory processor-readable medium of claim 15, wherein the stored processor-executable instructions are configured to cause the processor to perform operations further comprising:
- determining whether an energy measured in any of the two or more detector pixels is within a Compton gap of gamma ray photons incident on the pixel radiation detector; and
- ignoring or not recording the gamma ray detection events, which occurred in the two or more detector pixels in response to determining that the energy measured in any of the two or more detector pixels is within the Compton gap of gamma ray photons incident on the pixel radiation detector.

\* \* \* \* \*